United States Patent [19]
Chikama

[11] Patent Number: 5,961,445
[45] Date of Patent: Oct. 5, 1999

[54] ENDOSCOPE HAVING REPLACEABLE OBJECTIVE UNIT

[75] Inventor: Toshio Chikama, Tokyo, Japan

[73] Assignee: Machida Endoscope Co., Ltd., Tokyo, Japan

[21] Appl. No.: 08/967,451

[22] Filed: Nov. 11, 1997

Related U.S. Application Data

[63] Continuation of application No. 08/652,793, May 23, 1996, Pat. No. 5,711,756.

[30] Foreign Application Priority Data

May 31, 1995 [JP] Japan .................................. 7-156837

[51] Int. Cl.⁶ ........................................................ A61B 1/05
[52] U.S. Cl. ......................... 600/112; 600/129; 600/172; 600/175
[58] Field of Search ..................................... 600/112, 114, 600/129, 172, 175, 136, 138, 109

[56] References Cited

U.S. PATENT DOCUMENTS

| | | |
|---|---|---|
| 4,704,007 | 11/1987 | Landre et al. . |
| 4,777,524 | 10/1988 | Nakajima et al. . |
| 4,895,138 | 1/1990 | Yabe . |
| 4,918,521 | 4/1990 | Yabe et al. . |
| 5,051,824 | 9/1991 | Nishgaki . |
| 5,228,430 | 7/1993 | Sakamoto . |
| 5,379,756 | 1/1995 | Dileski et al. . |

FOREIGN PATENT DOCUMENTS

| | | |
|---|---|---|
| 0587513 | 3/1994 | European Pat. Off. . |
| 3600283 | 7/1986 | Germany . |
| 60-196718 | 10/1985 | Japan . |
| 3-69116 | 7/1991 | Japan . |

*Primary Examiner*—John P. Leubecker
*Attorney, Agent, or Firm*—Fish & Richardson P.C.

[57] ABSTRACT

An optical fibers bundle 30 for the use of illumination light transmission is received in a second receiving space 14 of an insert portion 10, and an objective unit 40 is received in a distal end portion of a first receiving space 13. A holder 60 is slidably inserted in the first receiving space 13. An image sensor 65 is supported on a distal end portion of the holder 60. Signal lines 66 from the image sensor 65 extends through the holder 60 and is introduced outside. The objective unit 40 and the holder 60 are threadingly connected with each other.

11 Claims, 17 Drawing Sheets

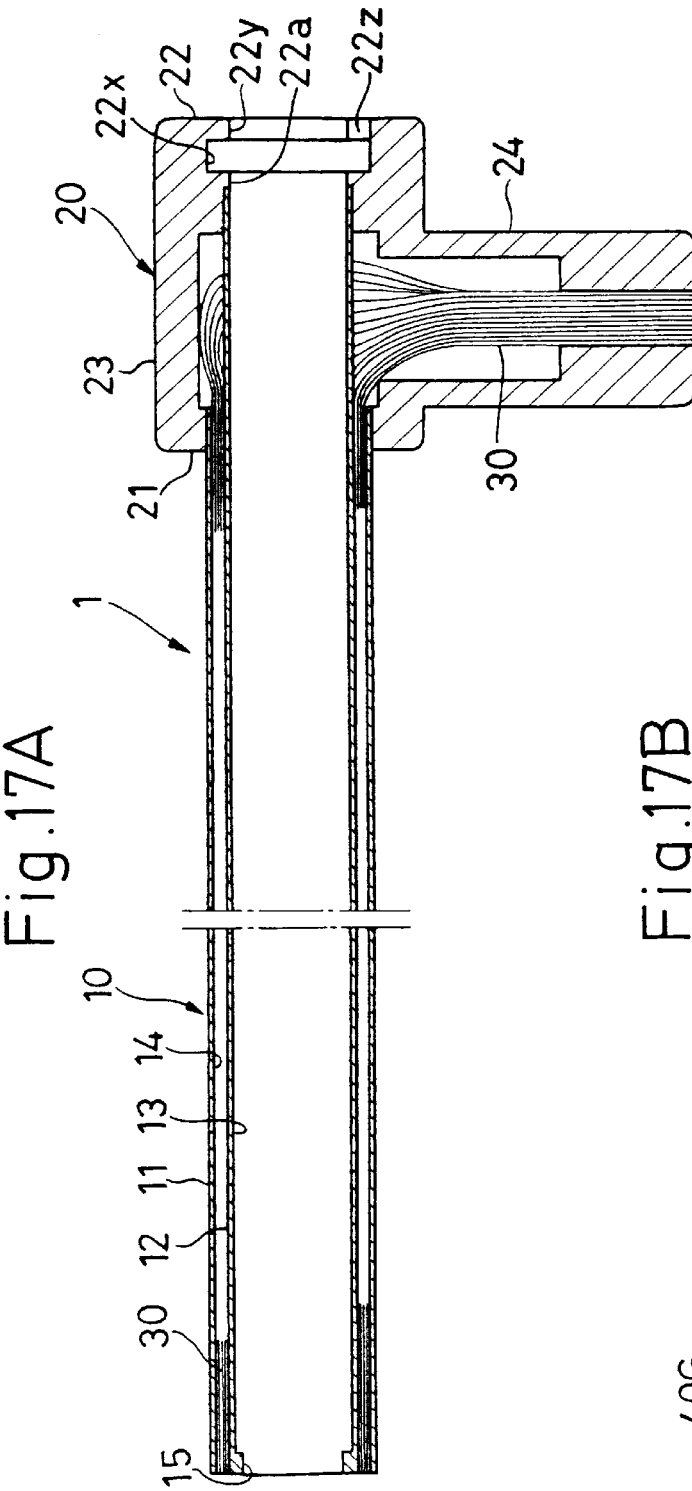
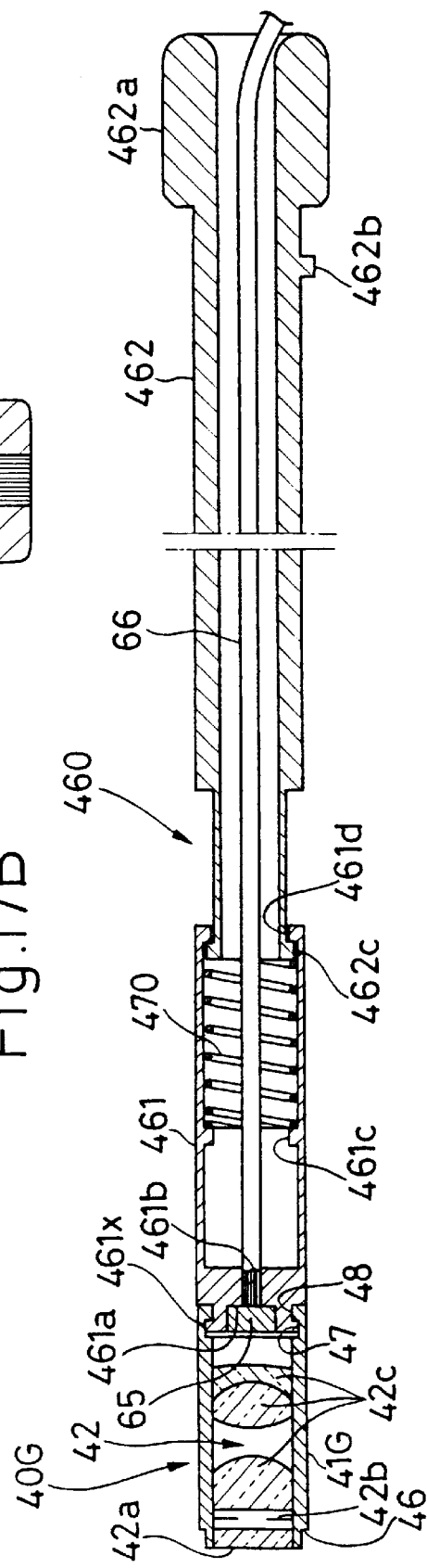

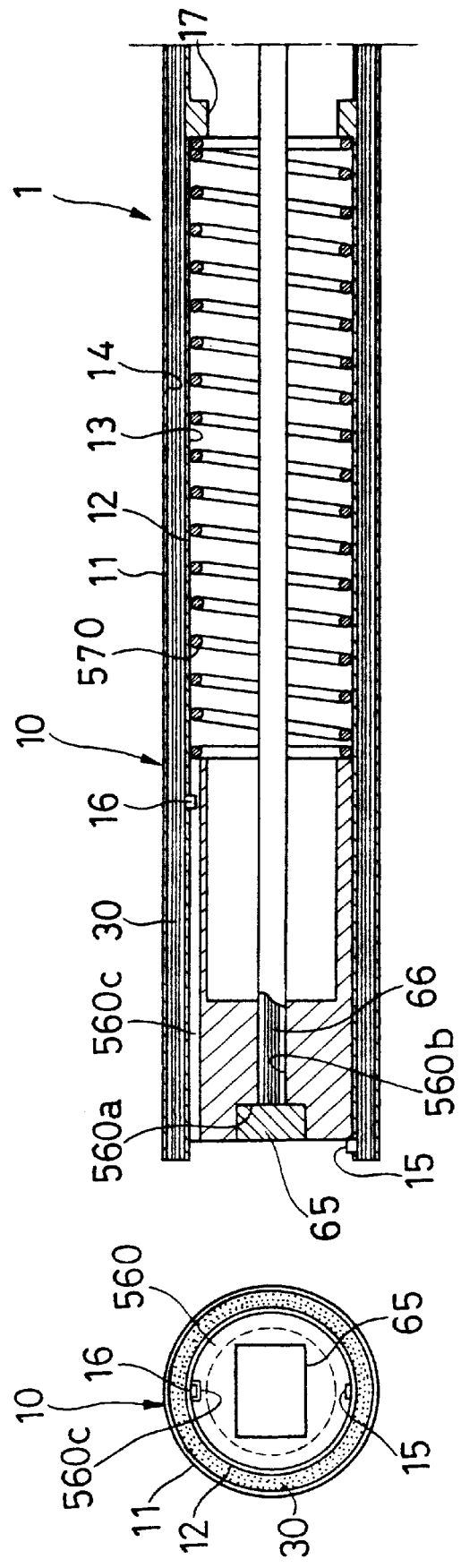

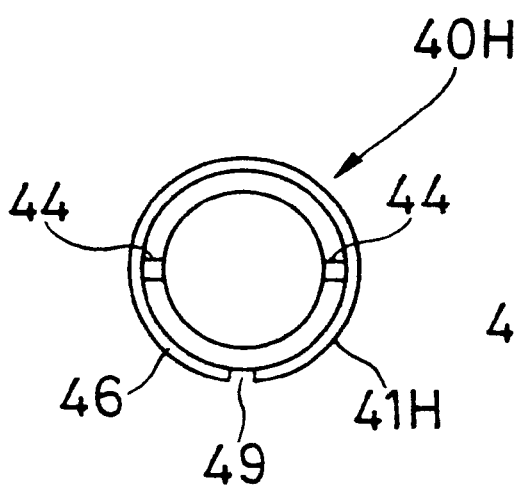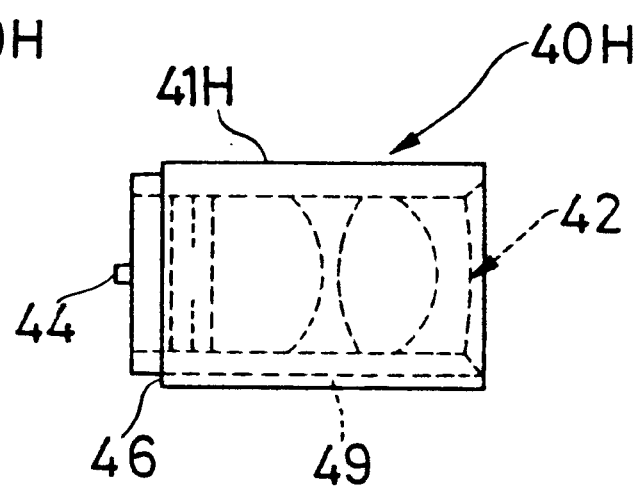

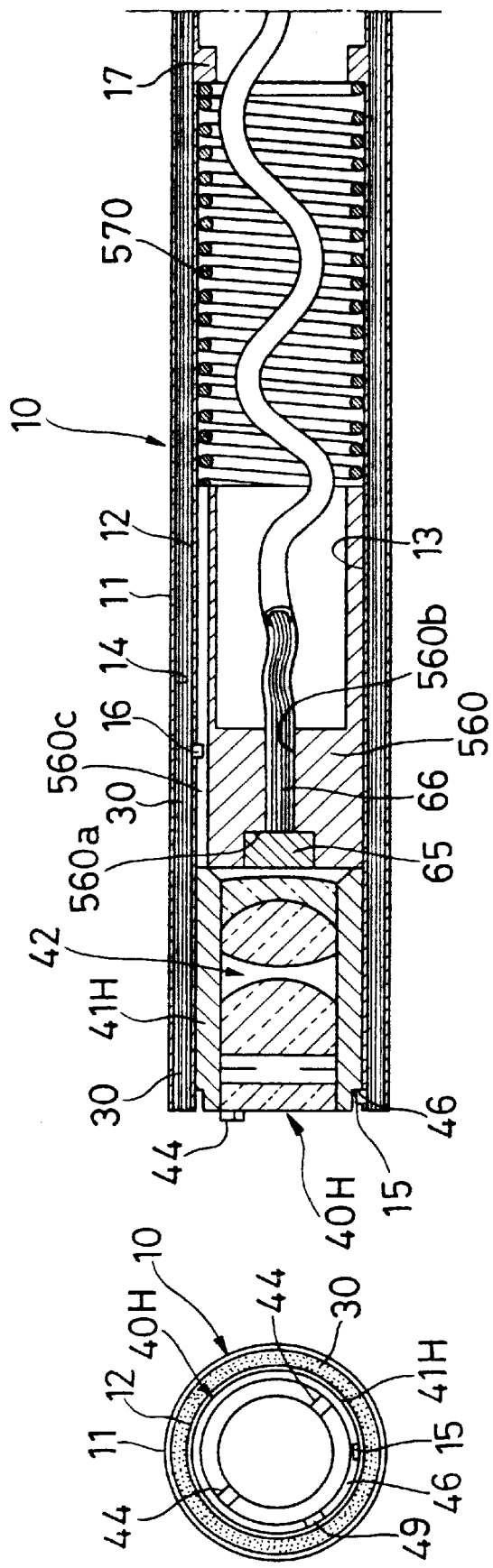

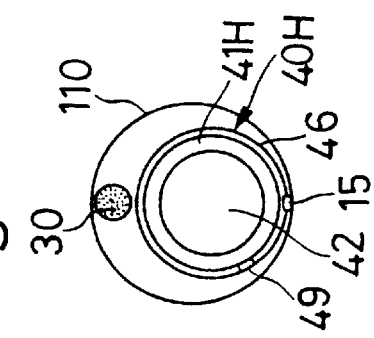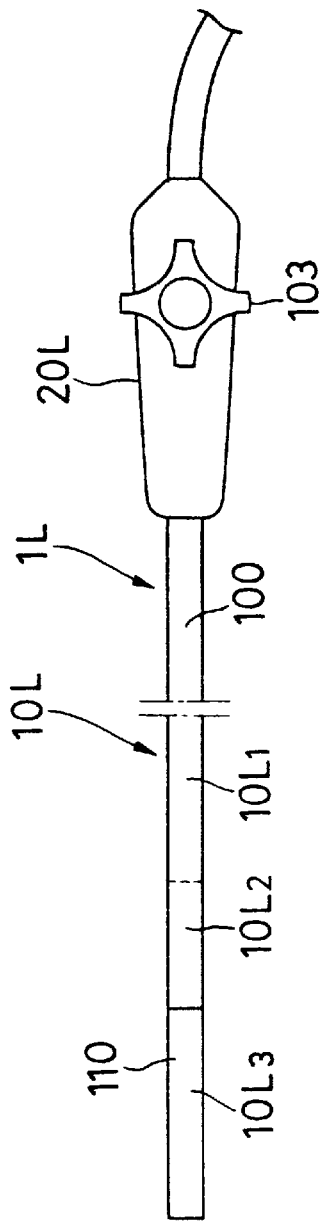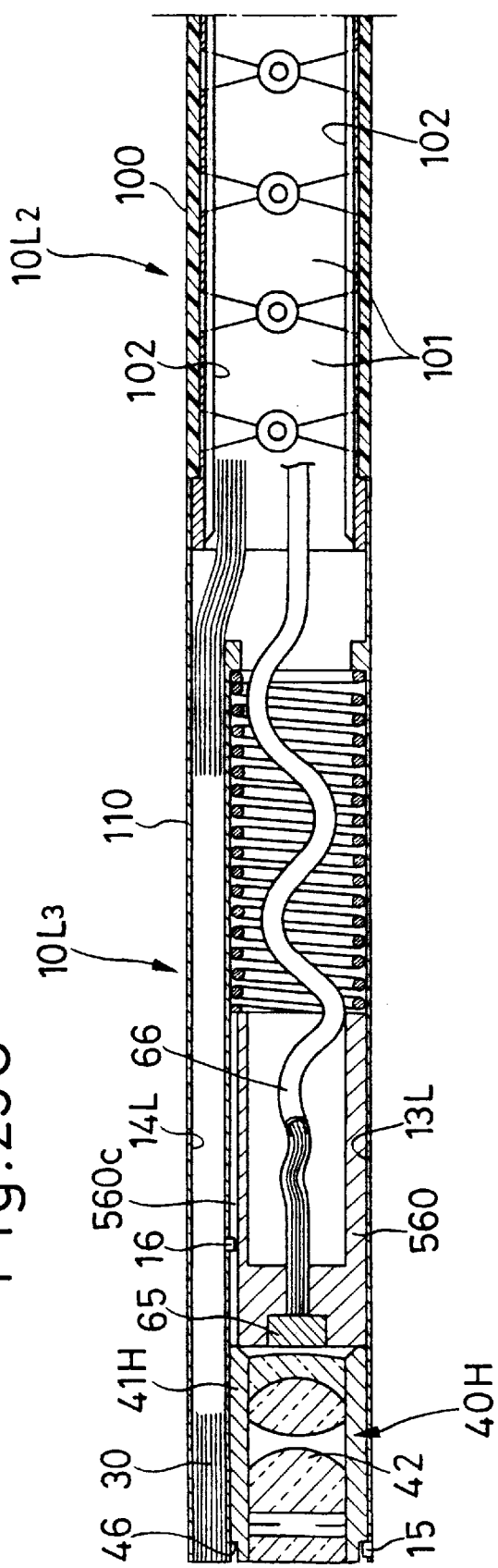

ENDOSCOPE HAVING REPLACEABLE OBJECTIVE UNIT

This is a continuing application of application Ser. No. 08/652,793, filed May 23, 1996, now U.S. Pat. No. 5,711,756.

BACKGROUND OF THE INVENTION

This invention relates to an endoscope in which an objective unit is replaceable.

As one example of such an endoscope, an electronic endoscope will be described. The endoscope includes a body having a hollow base portion, and a hollow insert portion extending through the base portion. An objective optical system is received in a distal end portion of the insert portion. An image sensor (light receiving means) such as a CCD or the like is disposed backwardly of the objective optical system. Signal lines (image transmission means) are connected to the image sensor. The signal lines extend through both the insert portion and the base portion and is introduced outside. A distal end portion of an optical fibers bundle (illumination light transmission means) is received in the distal end portion of the insert portion. This optical fibers bundle extends through both the insert portion and the body and is introduced outside. A rear end of the optical fibers bundle is connected to a light source device. Illumination light from the light source device passes through the optical fibers bundle and is irradiated from a distal end face of the optical fibers bundle at the distal end portion of the insert portion. An image of an observation object is taken by the image sensor through the objective optical system and an image signal thereof is transmitted to a processor through the signal lines. Then the image signal is converted to a television signal and displayed on a television set.

The endoscope of the type mentioned above is sometimes required to provide a wide angle view and a telescopic view. Also, the endoscope is required to provide different view fields such as a forward sight, a sideward sight, etc.

To meet with such requirements, if a plurality of endoscopes having different tasks are to be employed, the costs will be increased. In view of the foregoing, endoscopes are developed as disclosed in Japanese Patent Application Laid-Open No. 196718/1985 and Japanese Utility Model Application Laid-Open No. 69116/1991, in which an objective unit constituted of a sleeve-like support and an objective optical system received in the support is detachably attached to a distal end portion of an insert portion. In such endoscopes, interference between the objective optical system and illumination light transmission means is a problem to be solved. For example, as shown in FIG. 1 of Japanese Utility Model Application Laid-Open No. 69116/1991, illumination light from the illumination light transmission means is partly shaded by a support of an objective unit and as a consequence, the illumination light cannot be supplied over a wide range of area. On the contrary, if an arrangement is made such that a distal end of the optical fibers bundle projects forwardly of the objective optical system, the observation view field is shaded by the illumination light transmission means.

Accordingly, as disclosed in FIG. 2 of Japanese Utility Model Application Laid-Open No. 69116/1991 and Japanese Patent Application Laid-Open No. 196718/1985, the objective unit comprises not only an objective optical system but also a short optical fibers bundle used for illumination light transmission. The objective optical system and the optical fibers bundle are such arranged to have a positional relation that no interference occurs therebetween.

However, in the above-mentioned embodiment, since the objective unit has the objective lens and the optical fibers bundle incorporated therein, the construction becomes complicated and the manufacturing costs are increased. Further, the illumination light transmission means is split into a long optical fibers bundle on the insert portion side and the short optical fibers bundle on the objective unit side, and transmission losses of the illumination light occur at joint interfaces of both of them. In order to compensate the transmission losses, it is required that the optical fibers bundle is increased in sectional area. As a consequence, an outer diameter of the insert portion is increased. Furthermore, leak of light occurs at the joint interfaces and observation is interfered by that.

SUMMARY OF THE INVENTION

It is, therefore, an object of the present invention to provide an endoscope in which an objective unit is replaceable, and illumination light can be irradiated over a wide range of area without sacrificing its view field.

According to the invention, there is provided an endoscope comprising:

(a) a body including a hollow insert portion, the insert portion being elongate and having a hard distal end portion;

(b) illumination light transmission means whose distal end portion is disposed within the distal end portion of the insert portion and extending backwardly through the insert portion;

(c) an objective optical system disposed within the distal end portion of the insert portion;

(d) light receiving means disposed within the insert portion behind the objective optical system, and adapted to receive reflected light from an observation object via the objective optical system;

(e) image transmission means for backwardly transmitting image information received by the light receiving means, the image transmission means being inserted through the insert portion;

(f) an objective unit including the objective optical system, and a sleeve-like support for receiving and supporting the objective optical system, the objective unit being detachably supported within the distal end portion of the insert portion; and (g) retainer means for retaining the light receiving means within the insert portion, so that an axial position of the light receiving means is adjustable in accordance with an axial dimension of the objective unit.

BRIEF DESCRIPTION OF THE DRAWINGS

FIG. 17(A) is a vertical sectional view showing a body of an endoscope according to the eighth embodiment of the present invention, and FIG. 17(B) is a vertical sectional view showing a holder and an objective unit connected to the holder in the eighth embodiment;

FIG. 19(A) is a front view showing a distal end of an insert portion without being attached with an objective unit in the ninth embodiment of the present invention, and FIG. 19(B) is a vertical sectional view of the insert portion in the ninth embodiment;

FIG. 20(A) is a front view showing the distal end of the objective unit used in the ninth embodiment, and FIG. 20(B) is a side view of the objective unit in the ninth embodiment;

FIG. 21(A) is a front view showing the distal end of the insert portion attached with the objective unit in the ninth embodiment, and FIG. 21(B) is a vertical sectional view of the distal end portion attached with the objective unit in the ninth embodiment;

FIG. 23(A) is a side view of an endoscope according to an eleventh embodiment of the present invention, FIG. 23(B) is an enlarged front view of the distal end of the endoscope in the eleventh embodiment, and FIG. 23(C) is an enlarged vertical sectional view of the distal end of the endoscope in the eleventh embodiment.

DETAILED DESCRIPTION OF THE EMBODIMENTS

Figure 1:
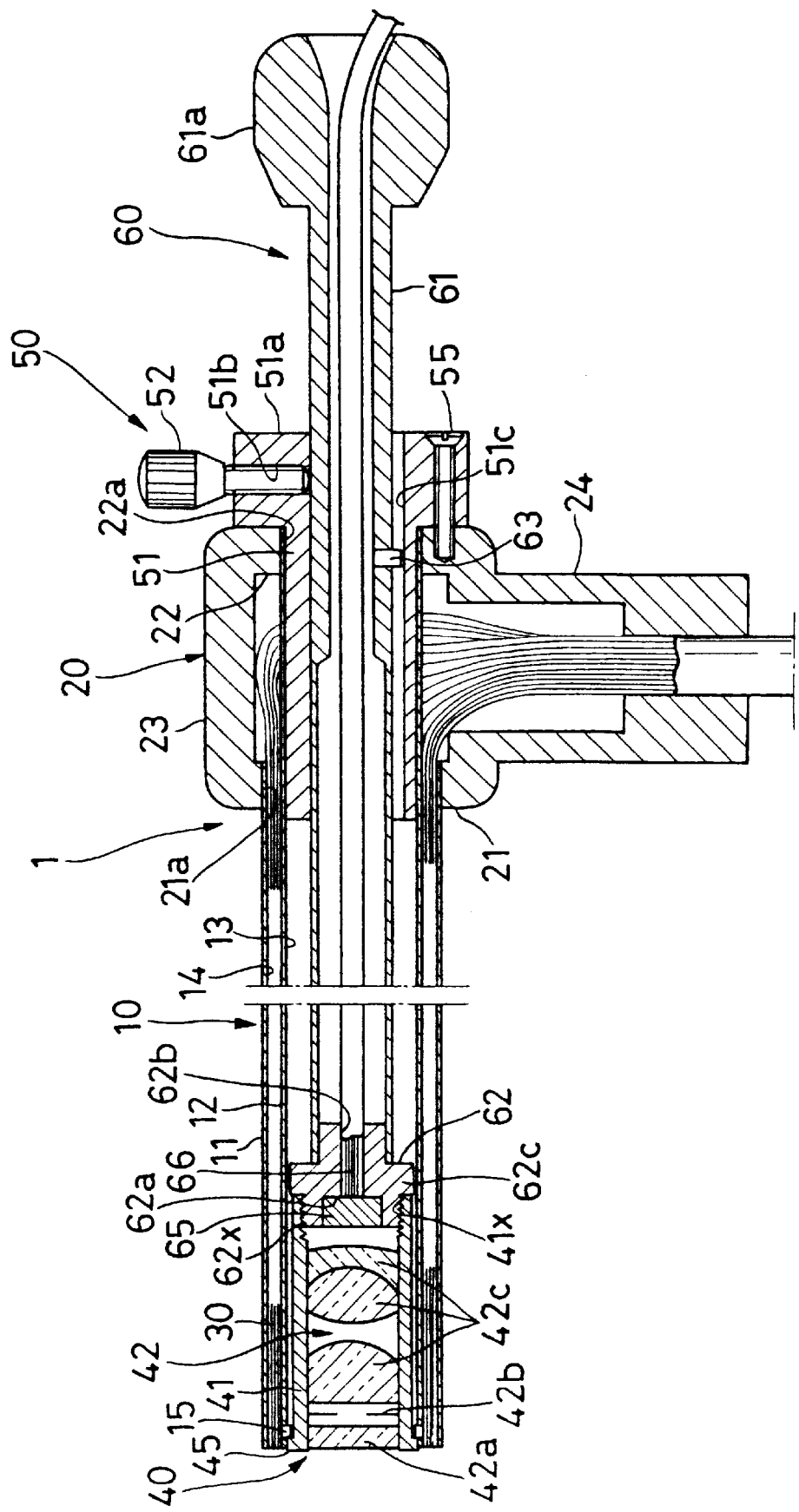
FIG. 1 is a vertical sectional view showing an endoscope attached with an objective unit according to the first embodiment of the present invention.

The first embodiment of the present invention will now be described with reference to FIGS. 1 through 4. FIG. 1 shows a hard endoscope. This hard endoscope includes a hollow body 1. The body 1 comprises a linearly extending insert portion 10 and a base portion 20 disposed on a rear end of the insert portion 10.

The insert portion 10 includes a hard outer tube 11 and a hard inner tube 12 which are coaxial with each other and have a circular shape in section. A distal end of the outer tube 11 is coincident with a distal end of the inner tube 12. An inner space of the inner tube 12 is provided as a first receiving space 13. An annular space between the outer tube 11 and the inner tube 12 coaxially surrounds the first receiving space 13 and is provided as a second receiving space 14.

The base portion 20 includes a front wall 21, a rear wall 22 parallel to the front wall 21, and a main sleeve portion 23 interconnecting the front and rear walls 21 and 22. A circular attachment hole 21a is formed in the front wall 21, whereas a circular attachment hole 22a is formed in the rear wall 22. The hole 21a is larger than the hole 22a. A rear end portion of the outer tube 11 is fixedly inserted into the attachment hole 21a of the front wall 21. A rear end portion of the inner tube 12 is allowed to extend through an internal space of the base portion 20 and fixedly inserted into the attachment hole 22a of the rear wall 22. The main sleeve portion 23 is connected with a radially extending auxiliary sleeve portion 24.

The second receiving space 14 receives therein an optical fibers bundle 30 (illumination light transmission means) for the use of illumination light transmission. The optical fibers bundle 30 extends axially. A distal end of the optical fibers bundle 30 is generally coincident with a distal end of the inner tube 12. The optical fibers bundle 30 extends from a rear end of the second receiving space 14 through the body 10, further through the auxiliary sleeve portion 24 and is introduced outside. A rear end of the optical fibers tube 30 is connected to a light source device.

A distal end portion of the first receiving space 13 receives therein an objective unit 40. This objective unit 40 includes a cylindrical support 41, and an objective optical system 42 received and supported in the support 41. The objective optical system 42 has a glass panel 42a, a diaphragm plate 42b, and a plurality (for example, three) of lenses 42c all arranged backwardly in this order from a distal end of the support 41. An annular engagement projection 45 is formed on and projects radially outwardly from an outer periphery of the distal end of the support 41. A single or a plurality of engagement projections 15 are formed on and projects radially inwardly from the inner tube 12 at locations somewhat retracted from the distal end of the inner tube 12. Engagement means is constituted by these engagement projections 45 and 15. That is, the engagement projection 45 of the support 41 is brought into abutment with the engagement projections 15 of the inner tube 12. As a consequence, the objective unit 40 is correctly positioned by being restricted in its backward movement. Owing to this arrangement, a distal end of the objective unit 40 is generally coincident with a distal end of the insert portion 10.

A cylindrical guide sleeve 51 is attached to the base portion 20. This guide sleeve 51 is inserted in the rear end portion of the inner tube 12, and constitutes a part of the base portion 20. A flange portion 51a is formed on a rear end of the guide sleeve 51. This flange portion 51a is secured to the rear wall 22 of the base portion 20 by a screw 55. A threaded hole 51b is formed in and radially extending all the way through the flange portion 51a. A screw 52 is threadingly engaged in the threaded hole 51a. Both the guide sleeve 51 and the screw 52 constitute fixture means 50 having the functions as later described.

A holder 60 (retainer means) is slidably inserted into the guide sleeve 51. The holder 60 has a hard tube 61 and a chip 62. The tube 61 extends through the guide sleeve 51 and further through the first receiving space 13 in such a manner as to be coaxial with the insert portion 10. A rear end portion of the tube 61 projects backwardly from the rear wall 22 of the base portion 20 and the guide sleeve 51. A handle portion 61a of an enlarged diameter is formed on the rear end portion of the tube 61. A rear end portion of the chip 62 is fixedly inserted into an opening at a distal end of the tube 61. The chip 62 has a recess 62a formed in a distal end face thereof and a through-hole 62b continuous with the recess 62 and extending through a rear end face thereof. The recess 62a receives therein an image sensor 65 (light receiving means) such as a CCD. Distal ends of signal lines (image transmission means) are connected to the image sensor 65. The signal lines 66 are allowed to extend through the hole 62b of the chip 62 and further through the tube 61 and introduced outside. Rear ends of the signal lines 66 are connected to a monitor television set through a processor.

An annular flange 62c is formed on an outer periphery of an intermediate portion of the chip 62. A male thread 62x is formed on an outer periphery of a distal end portion of the chip 62 and is threadingly engaged in a female thread 41x formed in an inner periphery of the rear end portion of the support 41 of the objective unit 40, so that the holder 60 and the objective unit 40 are connected together. In this way, connection means is constituted by the male thread 62x and the female thread 41x.

A distal end of the screw 52 is brought into abutment directly with an outer peripheral surface of the tube 61 and pushes the same as shown in FIG. 1. As a consequence, the holder 60 is detachably secured to the base portion 20. A key 63 is secured to the tube 61. This key 63 is received in an axially extending key groove 51c formed in an inner periphery of the guide sleeve 51.

Figure 2:
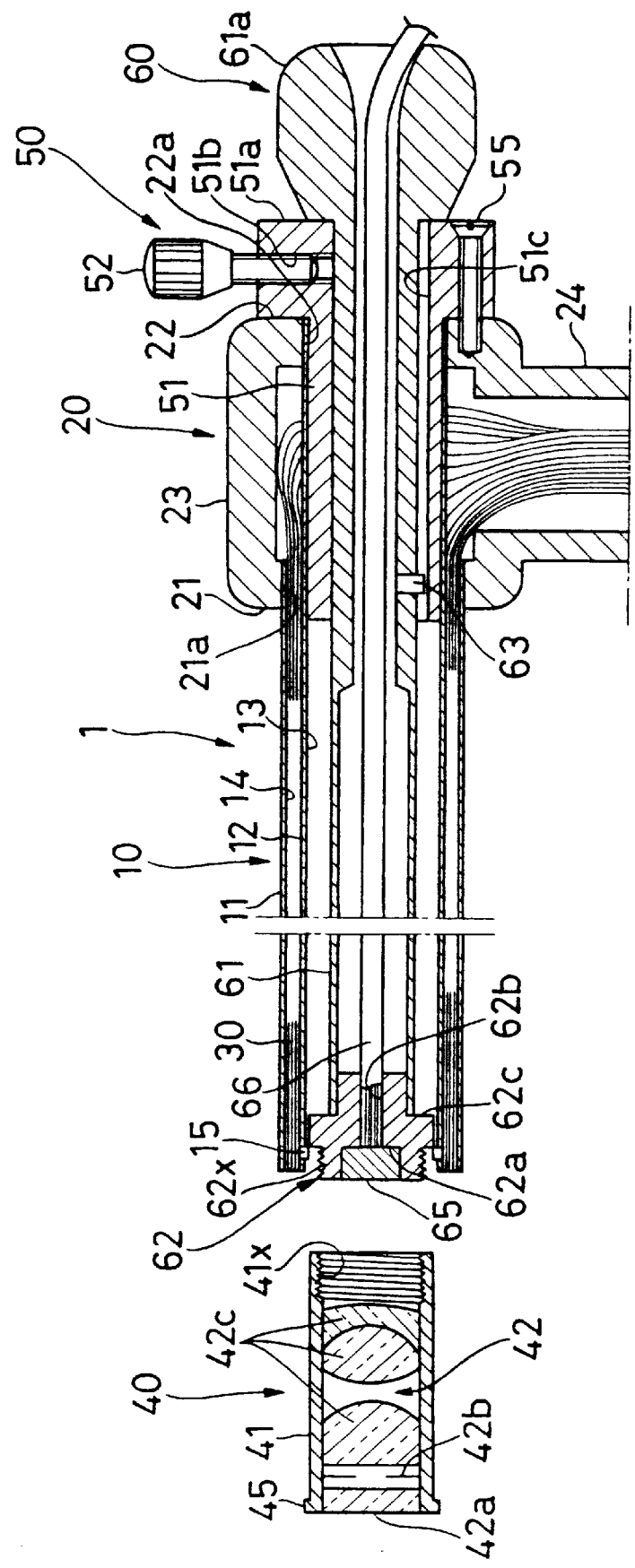
FIG. 2 is a vertical sectional view of the endoscope, not yet attached with the objective unit, in the first embodiment.

With the above construction, the objective unit 40 is detachable, namely replaceable, with respect to the insert portion 10 of the body 1. As shown in FIG. 2, in the state that the objective unit 40 is not yet attached, the holder 60 is moved forwardly relative to the body 1 until the handle portion 61a contacts the rear wall 22 of the base portion 20 and the chip 62 is located in an area in the vicinity of the distal end opening of the insert portion 10. In that state, the image sensor 65 is located at the distal end opening of the insert portion 10, so that dusts adhered to its light receiving surface can easily be wiped out.

For attaching the objective unit 40 to the insert portion 10, the screw 52 is loosened to make the holder slidable. In that state, the objective unit 40 is brought closer to the distal end of the holder 60, and the rear end portion of the support 41 is threadingly engaged with the distal end portion of the chip 62 and then inserted into the distal end opening of the first receiving space 13. At the time of this threading engagement, the rear end of the support 41 is brought into abutment with the flange portion 52c of the chip 62, so that the objective optical system 42 and the image sensor 65 are optically connected together in an appropriate positional relation. The threading engagement is achieved by rotating the objective unit 40. At that time, the holder 60 is prohibited from rotating by the key 63 and the key groove 51c.

Then, the holder 60 is slid backwardly. Before long, the engaging projection 45 at the distal end of the objective unit 40 is brought into abutment with the engagement projections 15 of the inner tube 12, so that the objective unit 40 and the image sensor 65 are prohibited from moving backwardly. In this way, the objective unit 40 and the image sensor 65 are correctly positioned. In that position, the screw 52 is screwed into the holder 60 for fixing it. In that correctly positioned state, the distal end of the objective unit 40 is generally coincident with the distal end of the insert portion 10 and also generally coincident with the distal end of the optical fibers bundle 30. For this reason, no cross interference occurs between the objective unit 40 and the optical fibers bundle 30. That is, no inconveniences for partly prohibiting the supply of illumination light, which would otherwise occur due to the objective unit 40 projecting forwardly of the distal end of the optical fibers bundle 30, and for reducing the view field, which would otherwise occur due to the objective unit 40 retracted further than the optical fibers bundle, are encountered.

For detaching the objective unit 40, the screw 52 is loosened to allow the holder 60 to move forwardly contrary to the above procedure, so that the objective unit 40 projecting from the distal end of the insert portion 10 is held by hand in order to remove the threading engagement relation with the holder 60.

Figure 3:
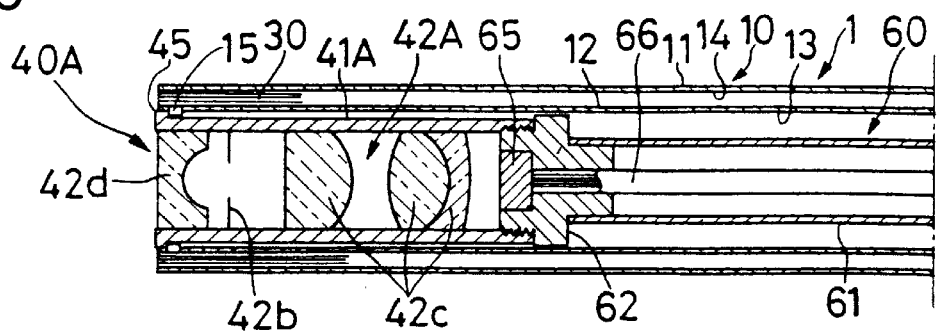
FIG. 3 is a vertical sectional view of a distal end portion of the endoscope attached with a different objective unit in the first embodiment.
Figure 4:
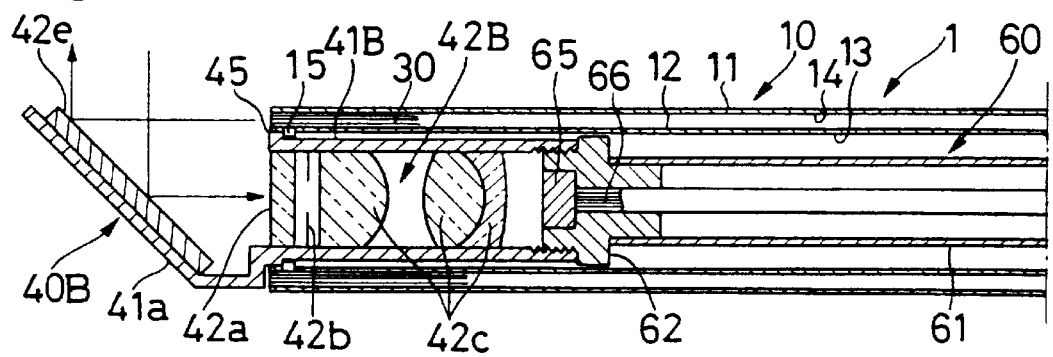
FIG. 4 is a vertical sectional view of a distal end portion of the endoscope attached with another different objective unit in the first embodiment.

Instead of the objective unit 40, objective units 40A and 40B shown respectively in FIGS. 3 and 4 may be attached to the body 1. In these objective units 40A and 40B, component parts corresponding to those of the objective unit 40 of FIGS. 1 and 2 are denoted by corresponding reference numeral and description thereof is omitted. The objective unit 40A of FIG. 3 is adopted in order to obtain a wide view field, and an objective optical system 42A has a concave lens 42d, instead of the glass panel 42a, at a distal end of a support 41A. An axial dimension of the objective unit 40A is longer than the objective unit 40 of FIGS. 1 and 2. Accordingly, when this objective unit 40A is attached, the image sensor 65 is more retracted from the distal end of the insert portion 10 than in the cases of FIGS. 1 and 2. Such an axial dimensional difference can be absorbed by sliding movement of the holder 60. The objective unit 40A is correctly positioned by engagement of the engagement projections 45 and 15 and the distal end of the objective unit 40A is brought to be coincident with the distal end of the insert portion 10. Accordingly, a possible occurrence of interference between the objective unit 40A and the optical fibers bundle 30 can be prevented.

The objective unit 40B of FIG. 4 is for the use of side view and has a bracket 41a on a distal end of a support 41B. The objective optical system 40B has a mirror 42e (reflection surface for changing the optical axis) attached to the bracket 41a and inclined by 45 degrees with respect to the axis of the insert portion 10. In this embodiment, illumination light outgoing from the distal end of the optical fibers bundle 30 is reflected by the mirror 42e and progresses radially so as to be supplied to an observation object. Reflecting light from the observation object is reflected on the mirror 42e and allowed to pass through the objective optical system 42B so as to be supplied to an image sensor 65. This objective unit 40B is also attached in the same way as the afore-mentioned objective units 40 and 40A, and a possible occurrence of interference between the objective optical system 42 and the optical fibers bundle 30 can be prevented. Since the illumination light prohibited by the bracket 41a is only the illumination light output from a part of the distal end portion of the optical fibers bundle 30, no significant inconveniences are encountered.

Other embodiments of the present invention will now be described. In these embodiments, component parts corresponding to those of the preceding embodiment are denoted by corresponding reference numeral and description thereof is omitted.

Figure 5:
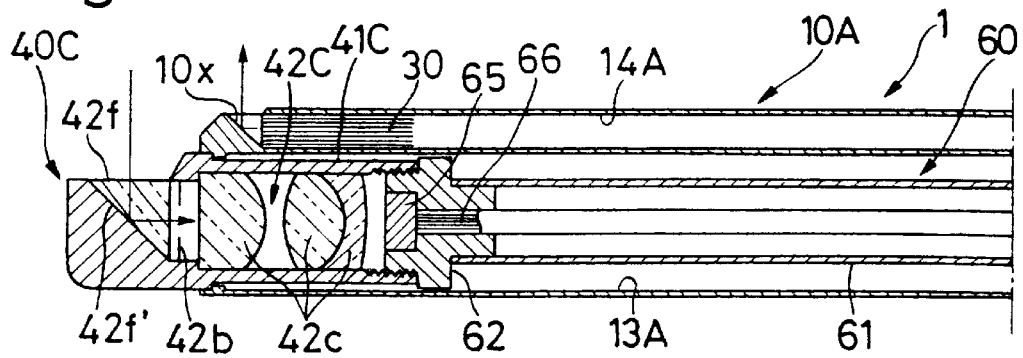
FIG. 5 is a vertical sectional view of a distal end portion of an endoscope attached with an objective unit according to the second embodiment.
Figure 6:
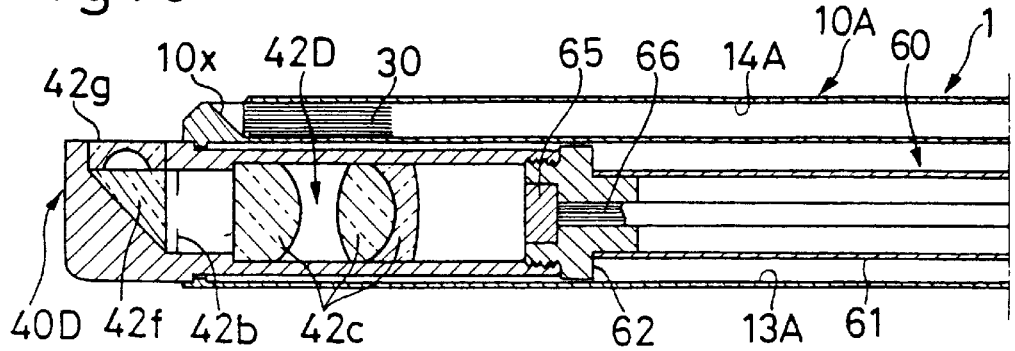
FIG. 6 is a vertical sectional view of a distal end portion of the endoscope attached with a different objective unit in the second embodiment.

FIGS. 5 and 6 show the second embodiment of the present invention. An endoscope employed in this embodiment is a side view specific endoscope. In this endoscope, an insert portion 10A is not of a double tube construction, and a first receiving space 13A and a second receiving space 14A are formed in an elongated hard member in spaced parallel relation to each other. These receiving spaces 13A and 14A are offset in opposite directions from a center axis of the insert portion. In the embodiment, the insert portion 10A is fixedly inserted into a front wall of a base portion not shown. Formed on a distal end of the insert portion 10A is a mirror 10x (reflection surface) faced with a distal end opening of the second receiving space 14A and inclined by 45 degrees with respect to an axis of the insert portion 10A. Illumination light outgoing from a distal end of an optical fibers bundle 30 is reflected on the mirror 10x so as to proceed radially. A holder 60 has the same construction as that in the above embodiment. The holder 60 is slidable relative to the base portion and secured to the base portion by a guide sleeve and a screw.

An objective optical system 42C of an objective unit 40C has a prism 42f at a distal end portion of the support 41C. This prism 42f projects forwardly of the distal end of the insert portion 10A. Reflecting light from the observation object is reflected on a reflection surface 42f' of the prism 42f so as to proceed towards lenses 42c.

An objective optical system 42D of an objective unit 40D of FIG. 6 has a concave lens 42g on an incident side of the prism 42f at the distal end portion of a support sleeve 41D and offers a wide angle view. The objective unit 40D is longer in axial dimension than the objective unit 40C. Any difference in axial dimension between the objective units 40C and 40D can be absorbed by sliding movement of the holder 60. Distal ends of the objective units 40C and 40D can be held in the same positional relation with respect to the distal end of the insert portion 40, the distal end of the optical fibers bundle 30 and the mirror 16 under the engagement function of the engagement projections 15 and 45. As a consequence, a relation between an irradiating position of illumination light and an incident position thereof to the objective optical systems 42C and 42D can be arranged to be a constant and appropriate one. Thus, a possible occurrence of cross interference between the optical fibers bundle 30 and the objective optical system can be eliminated.

Figure 7A:
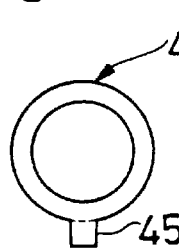
FIG. 7(A) is a front view showing a distal end of an objective unit used in the third embodiment of the present invention.
Figure 7B:
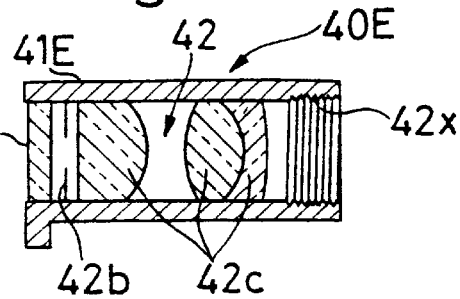
FIG. 7(B) is a vertical sectional view thereof.
Figure 8A:
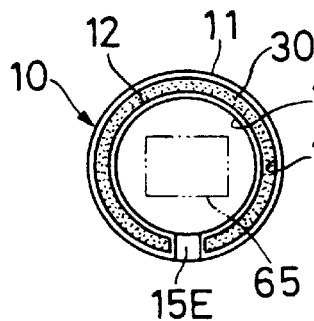
FIG. 8(A) is a front view showing a distal end of an insert portion, without being attached with the objective unit, in the third embodiment.
Figure 8B:
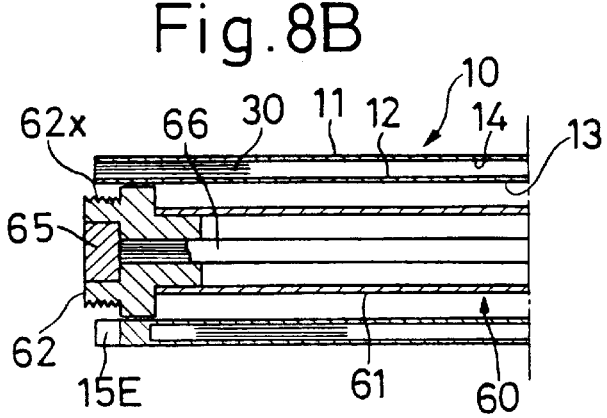
FIG. 8(B) is a vertical sectional view thereof.
Figure 9:
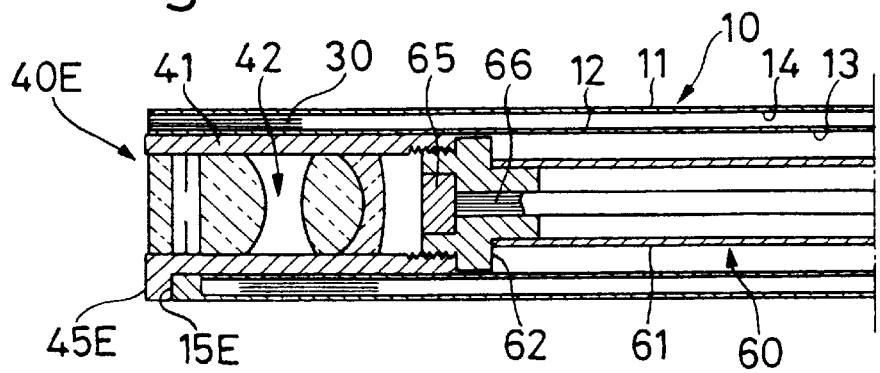
FIG. 9 is a vertical sectional view of the distal end portion of the insert portion attached with the objective unit, in the third embodiment.

FIGS. 7 through 9 show the third embodiment. As shown in FIG. 7, A radially outwardly projecting engagement projection 45E is formed on an outer periphery of a distal end of a support 41E of an objective unit 40E. This engagement projection 45E is not annular and partly formed. On the other hand, as shown in FIG. 8, an engagement recess 15E is formed in a distal end of an inner tube 11 of an insert portion 10. As shown in FIG. 9, the engagement projection 45E is fitted in the engagement recess 15E so that the objective unit 40E is restricted from moving backwardly and axially correctly positioned. Also, the objective unit 40E is prevented from rotation.

Figure 10:
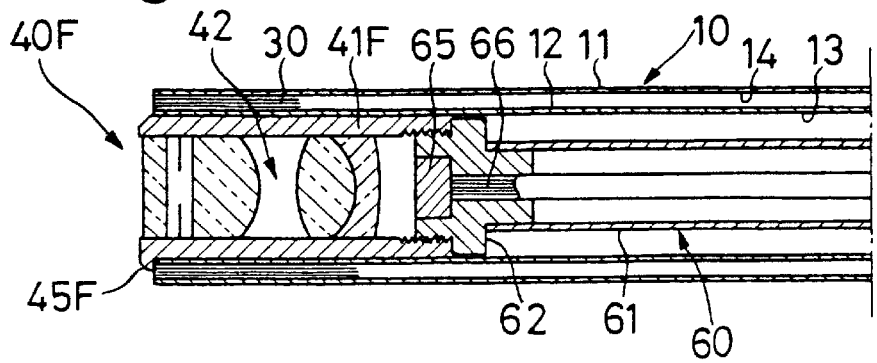
FIG. 10 is a vertical sectional view of a distal end portion of an endoscope attached with an objective unit according to the fourth embodiment of the present invention.

In the fourth embodiment shown in FIG. 10, a radially outwardly extending small engagement projection 45F is formed on an outer periphery of a distal end of a support 41F of an objective unit 40F. This engagement projection 45F is not annular and partly formed. The engagement projection 45F is brought into engagement with a distal end face of an insert portion 10 so that the objective unit 40F is restricted from moving backwardly and axially correctly positioned.

Figure 11:
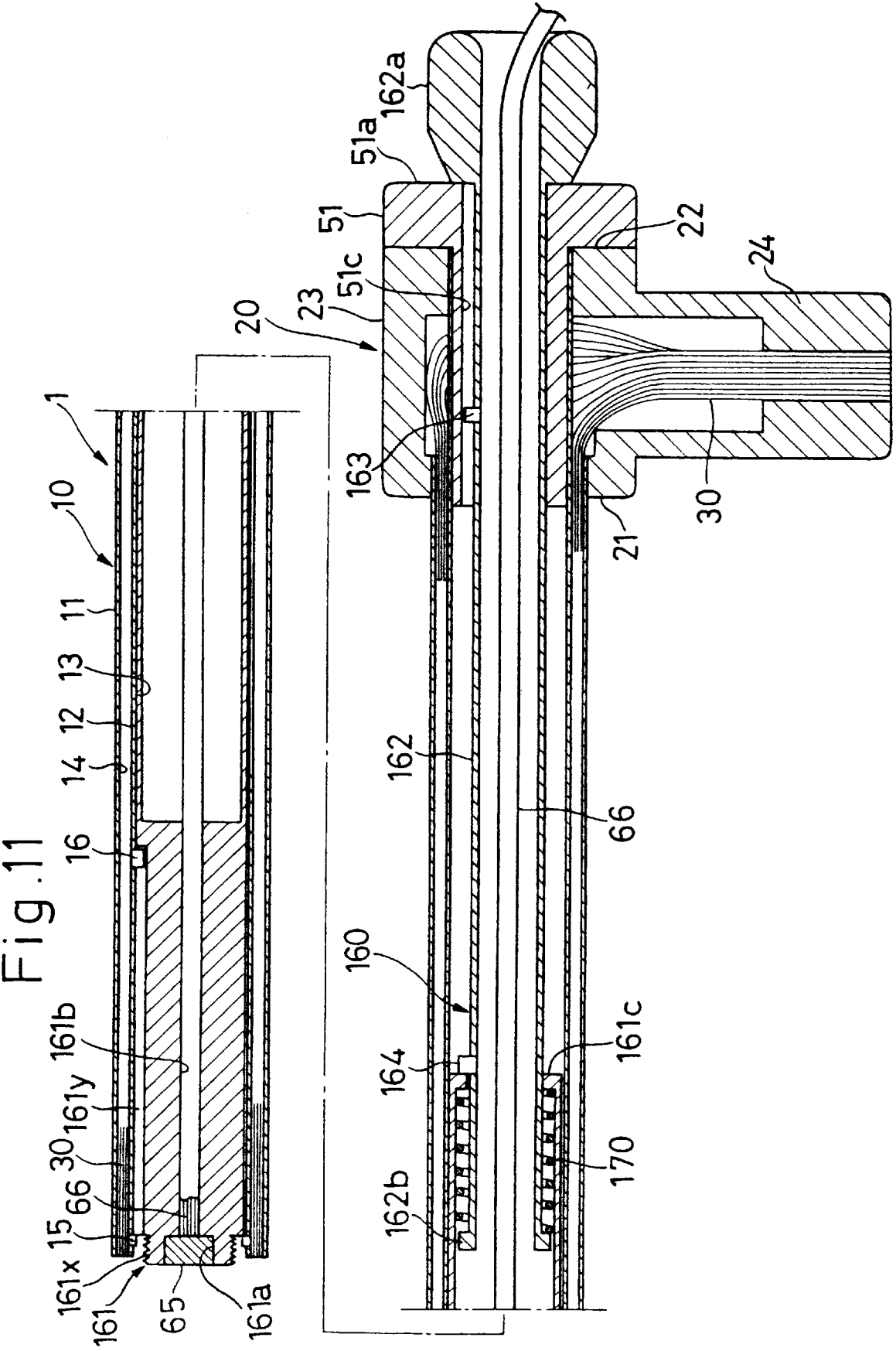
FIG. 11 is a vertical sectional view of an endoscope without being attached with an objective unit according to the fifth embodiment of the present invention.
Figure 12:
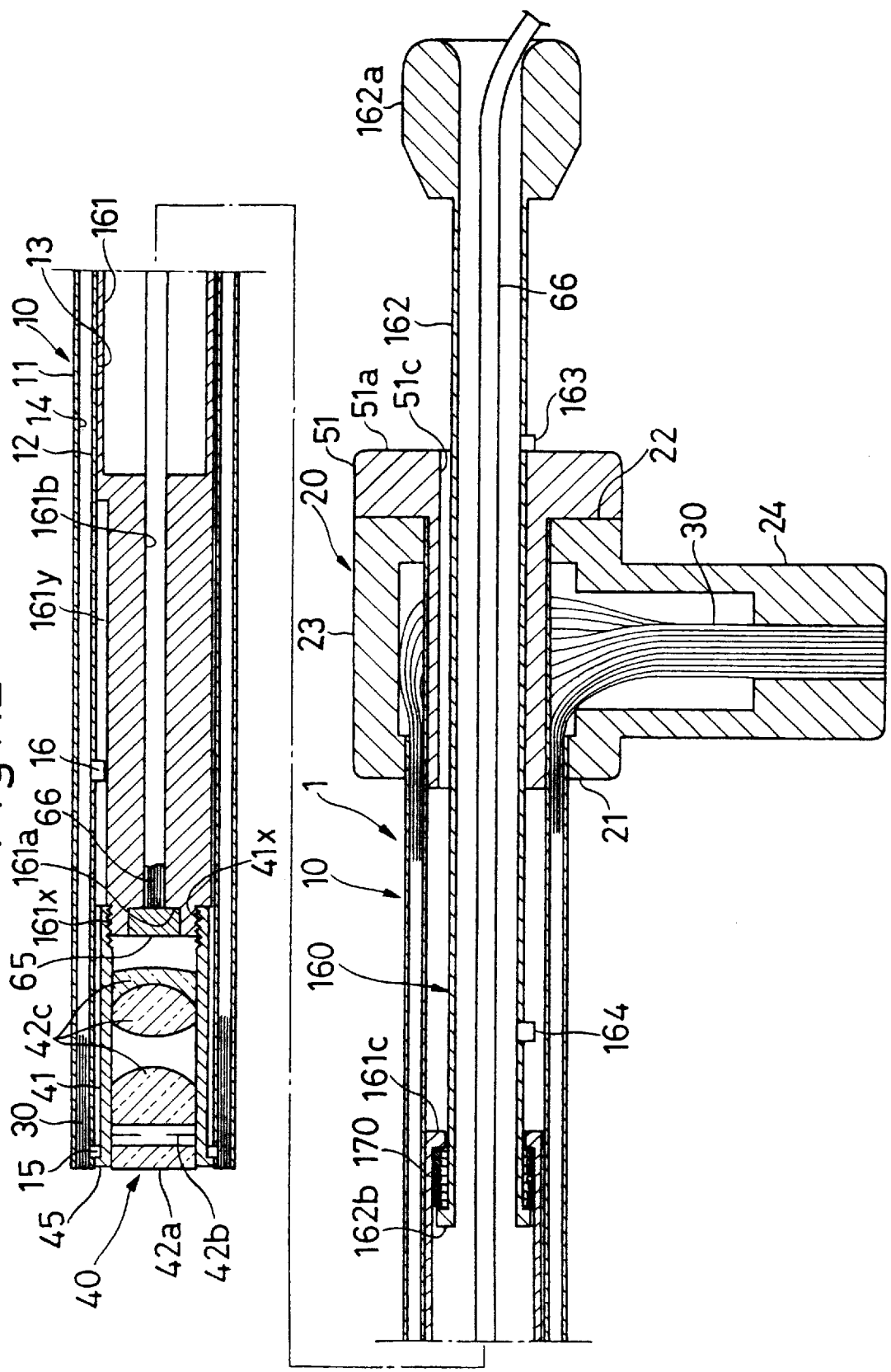
FIG. 12 is a vertical sectional view of the endoscope attached with the objective unit in the fifth embodiment.

The fifth embodiment shown in FIGS. 11 and 12 is different from the first embodiment of FIGS. 1 and 2 only in the respect of a construction of a holder 160 (retainer means). That is, this holder 160 includes a first tube 161 (first holder member) disposed on a front part of a body 10 and a second tube 162 (second holder member) disposed on a rear part of the body 10. The first tube 161 has a recess 161a for receiving therein an image sensor 65 which recess 161 is formed on a distal end face the first tube 161, and a passage hole 161b for allowing the passage of signal lines 66. A distal end portion of the first tube 161 is reduced in diameter, and has a male thread 161x formed on an outer periphery thereof. An axially extending key groove 161y is formed in the outer periphery of the first tube 161 at location backwardly of the male thread 161x. A radially inwardly projecting key 16 is formed on an inner tube 12. This key 16 is received in the key groove 161y.

A radially inwardly extending annular spring retainer 161c is formed on a rear end of the first tube 161. The second tube 162 is smaller in diameter than the first tube 161. A radially outwardly projecting annular spring retainer 162b is formed on a distal end of the second tube 162. A coil spring 170 is interposed between an inner peripheral surface of the rear end portion of the first tube 161 and an outer peripheral surface of the distal end portion of the second tube 162. This coil spring 170 is in a compressed state and opposite ends of the coil spring 170 are retained by the spring retainers 161c and 162b.

The second tube 162 is pierced into a guide sleeve 51. A handle 162a of an enlarged diameter is formed on a rear end of the second tube 162. An engagement projection (second engagement means) 163 to be passed through a passage groove 51c of the guide sleeve 51 is disposed at a location in the vicinity of the rear end of the second tube 162, whereas a radially outwardly projecting pressure projection 164 is disposed at a location in the vicinity of the distal end of the second tube 162.

With the above construction, in a state that the objective unit 40 is not yet attached, the second tube 162 is in a location, namely in a forward location, with the handle portion 162a abutted with a flange portion 51a of the guide sleeve 51. At that time, since the pressure projection 164 pushes the first tube 161, the first tube 161 is also in the forward location and an image sensor 65 is exposed outside for easy cleaning. In that state, the engagement projection 163 is received in the passage groove 51c.

Then, the objective unit 40 is threadingly engaged with a male thread 161x of the first tube 161. At that time, since the key 16 of the inner tube 12 is inserted in the key groove 161y of the first tube 161, the first tube 161 is prohibited from rotation. As a consequence, by rotating the objective unit 40, the above threading engagement can be progressed. After the completion of the above threading engagement, the handle portion 162a of the second tube 162 is pulled to retract the second tube 162. As a consequence, the engagement projection 163 of the second tube 162 is disengaged from the passage groove 51c. In that state, the second tube 162 is rotated by 180 degrees to bring the engagement projection 163 into engagement with the a rear end face of the guide sleeve 51. As the second tube 162 is retracted, the first tube 162 associated with the second tube 162 through the coil spring 170 is also retracted. Before long, the engagement projection 45 (first engagement means) of the objective unit 40 is brought into engagement with the engagement projection 15 of the inner tube 12, so that the objective unit 40 and the first tube 161 are restricted from moving backwardly and the objective unit 40 is correctly positioned.

In that state, the coil spring 170 is in a compressed state and thus tends to reduce the entire length of the holder 160. That is, the first tube 161 is biased backwardly and the second tube 162 is biased forwardly. The first tube 161 is restricted from moving backwardly by the engagement of the engagement projections 15 and 45, and the second tube 162 is restricted from moving forwardly by the engagement of the engagement projection 163 with the rear surface of the guide sleeve 51. As a consequence, the first and second tubes 161 and 162 are supported in the above engagement position in a stable manner.

In the endoscope of the fifth embodiment, the objective units 40A and 40B can also be attached instead of the objective unit 40. Any axial dimensional difference of these objective units can be absorbed by axial movement of the first tube 161 accompanied with variation of the length of the coil spring 170, and the objective unit can correctly be positioned in a predetermined location.

Figure 13:
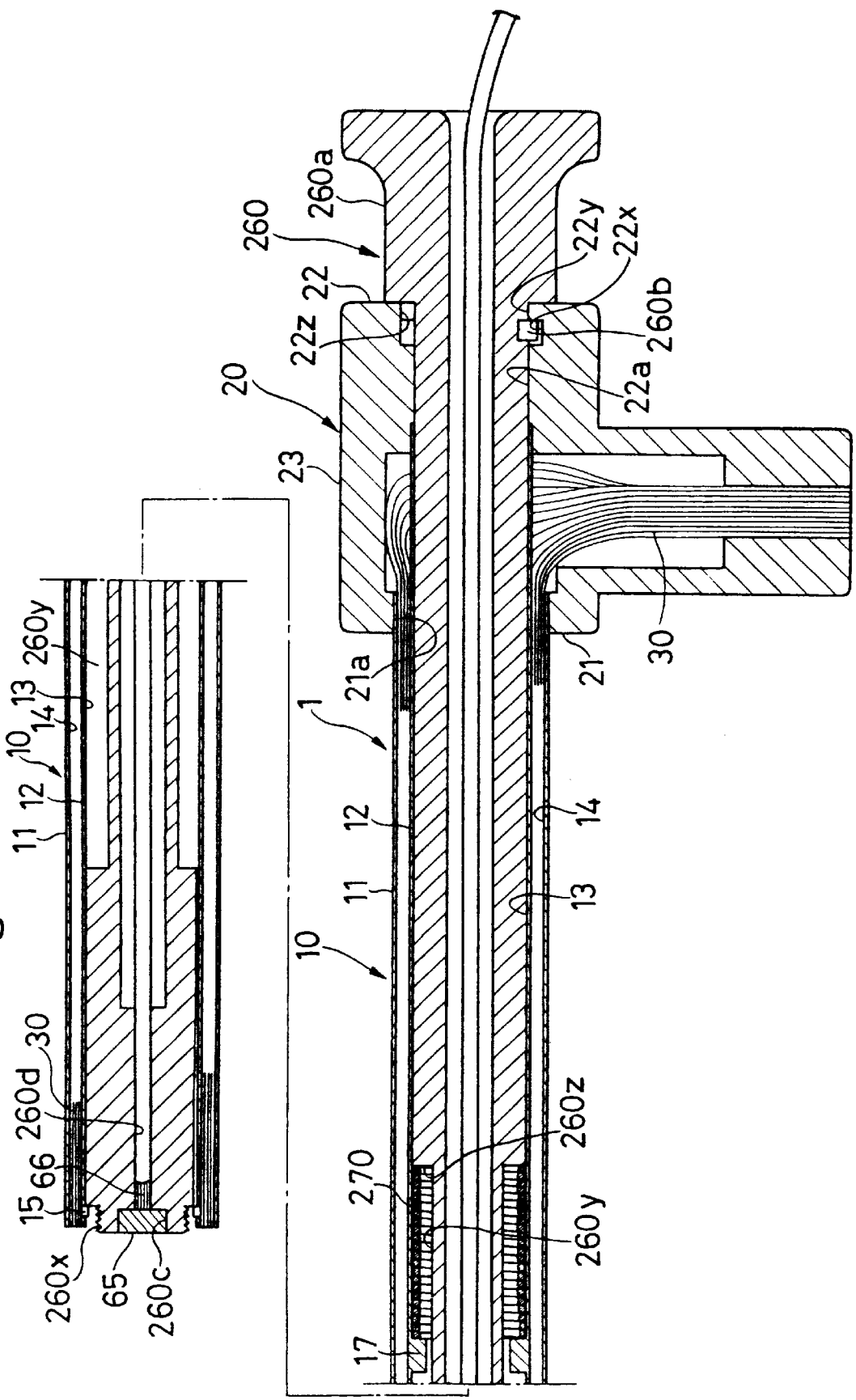
FIG. 13 is a vertical sectional view of an endoscope without being attached with an objective unit according to the sixth embodiment of the present invention.
Figure 14:
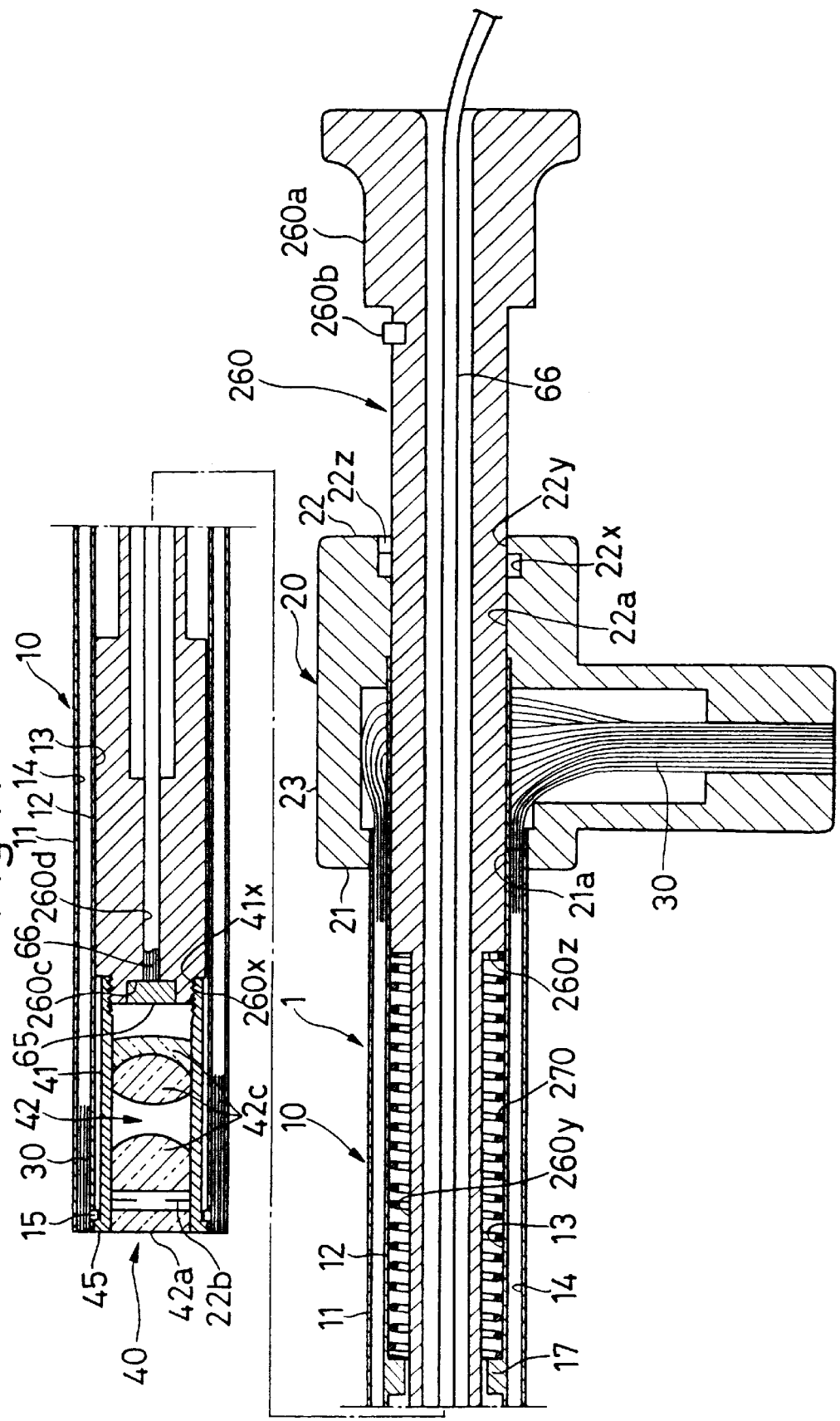
FIG. 14 is a vertical sectional view of the endoscope attached with the objective unit in the sixth embodiment.

In the sixth embodiment shown in FIGS. 13 and 14, a holder 260 (retainer means) is formed of a tube and has a handle portion 260a disposed on a rear end thereof. An engagement projection 260b is disposed at a location in the vicinity of the handle portion 260a. This engagement projection 260b can be received in an annular groove 22x formed in an inner peripheral surface of an attachment hole 22a of a base portion 20. An axially extending passage groove 22z is formed in an annular engagement projection 22y adjacent to the annular groove 22x.

The holder 260 further includes a recess 260c for receiving therein an image sensor 65 which recess 260c is formed on a distal end face of the holder 260, and a hole 260d for allowing the passage of signal lines 66. A distal end portion of the holder 260 is reduced in diameter and a male thread 260x is formed on an outer periphery thereof. An annular recess 260y is formed in an intermediate portion of the holder 260, and a coil spring 270 is received in this recess 260y. A rear end of the recess 260y has an annular step and serves as a spring retainer 260z.

A radially and inwardly projecting annular spring retainer 17 is formed on an intermediate portion of the inner tube 11. The coil spring 270 is in a compressed state, and opposite ends thereof are retained respectively by the spring retainers 160z and 17.

With the above construction, in the state that the objective unit 40 is not yet attached, the holder 260 is in a location with the handle portion 260a abutted with a rear face of the base portion 20 and the image sensor 65 is exposed outside. At that time, the engagement projection 260b of the holder 260 is received in the annular groove 22x of the base portion 20 and retained by the engagement projection 22y. The holder 260 is prohibited from moving backwardly against a biasing force of the coil spring 270.

Then, the objective unit 40 is threadingly engaged with the male thread 260x of the holder 260. After the completion of this threading engagement, the holder 260 is rotated so that the engagement projection 260b is coincident with the passage groove 22z. Owing to this arrangement, the holder 260 is moved backwardly by the biasing force of the coil spring 270. Then, the engagement projection 45 of the objective unit 40 is retained by the engagement projection 15 of the inner tube 12, so that the objective unit 40 and the holder 260 are prohibited from moving backwardly, and the objective unit 40 is correctly positioned.

In that state, the coil spring 270 is in a compressed state and serves to normally bias the holder 260 backwardly. The holder 260 is supported in the above-mentioned engagement position in a stable manner because the backward movement of the holder 260 is restricted by engagement between the engagement projections 15 and 45.

In the endoscope of the sixth embodiment, the objective units 40A and 40B shown in FIGS. 3 and 4 can also be attached instead of the objective unit 40. Any axial dimensional difference of these objective units can be absorbed by axial movement of the holder 260 accompanied by variation of the length of the coil spring 270, and the objective unit can correctly be positioned in a predetermined location.

Figure 15:
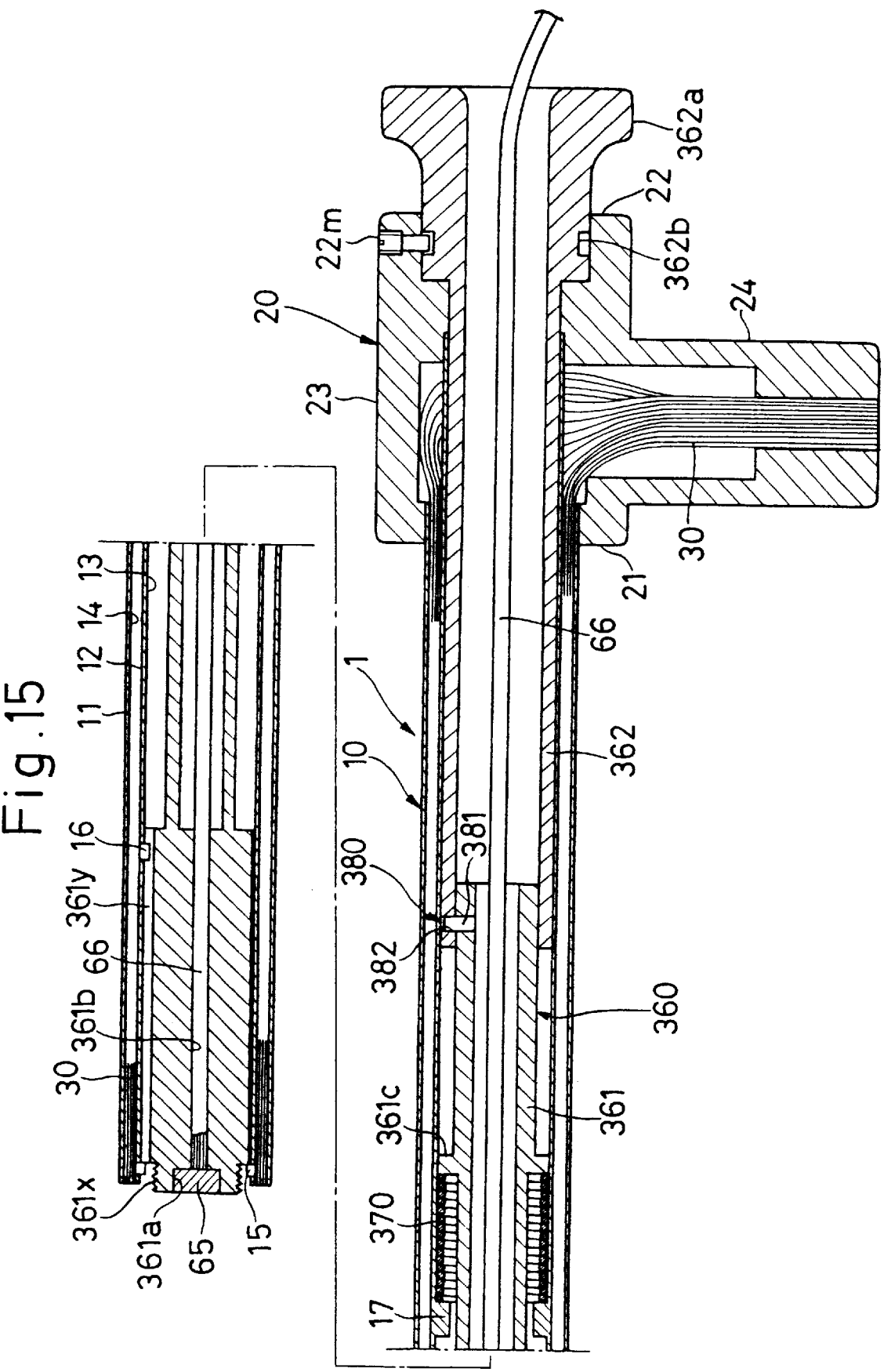
FIG. 15 is a vertical sectional view of an endoscope without being attached with an objective unit according to the seventh embodiment of the present invention.
Figure 16:
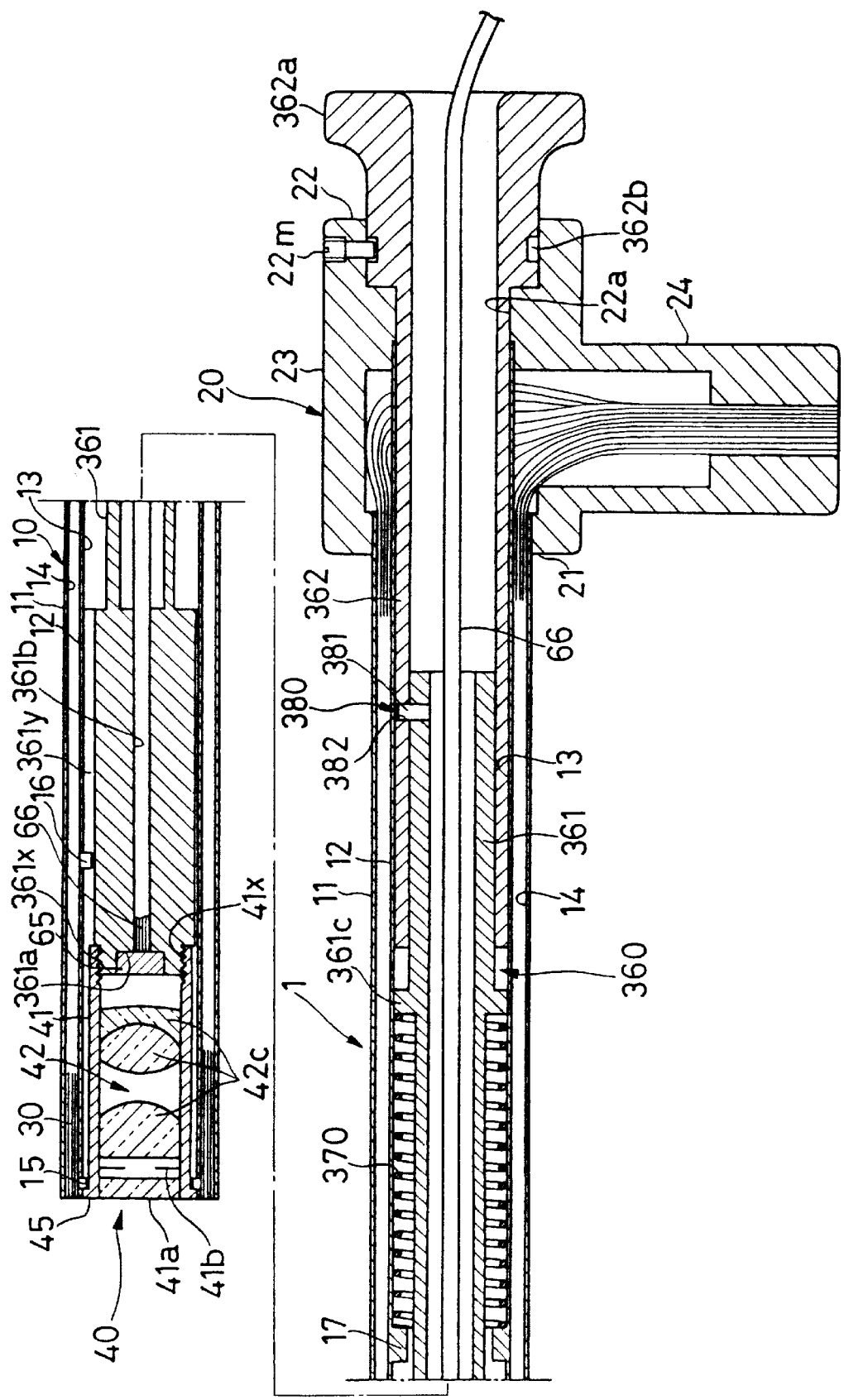
FIG. 16 is a vertical sectional view of the endoscope attached with the objective unit in the seventh embodiment.

In the seventh embodiment shown in FIGS. 15 and 16, a holder 360 (retainer means) includes a first tube 361 (first holder member) disposed at a front portion of the body 10, and a second tube 362 (second holder member) disposed at a rear portion of the body 10. The first tube 361 includes a recess 361a for receiving therein an image sensor 65 which recess 361a is formed on a distal end face of the first tube 361, and a hole 361b for allowing the passage of signal lines 66. A distal end portion of the first tube 361 is reduced in diameter, and a male thread 361x is formed in an outer periphery thereof. A key groove 361y is formed in the outer periphery of the first tube 361 at a location backwardly of the male thread 361x. A radially inwardly extending annular spring retainer 361c is formed at a location a predetermined distance this way from the rear end of the first tube 361. A radially inwardly projecting key 16 is formed on the inner tube 12 and this key 16 is received in the key groove 361y. A radially inwardly projecting annular spring retainer 17 is formed on the inner tube 12, and a coil spring 370 is interposed between the spring retainers 361c and 17.

The second tube 362 is pierced into the base portion 20. A handle portion 362a of an enlarged diameter is formed on the rear end of the second tube 362, and an annular groove 362b is formed in this handle portion 362a. A screw 22m threadingly progressed into the base portion 20 is inserted into the annular groove 362b, so that the second tube 362 can make only a rotation and is prohibited from moving axially. A rear end portion of the first tube 361 is inserted into the distal end portion of the second tube 362 and associated with each other through a cam mechanism 380. This cam mechanism 380 includes a radially outwardly projecting pin 381 (projection) mounted on the rear end portion of the first tube 361, and a spiral groove 382 formed in a peripheral wall of the distal end portion of the second tube 362.

With the above construction, in the state that the objective unit 40 is not yet attached, the pin 381 of the first tube 361 is disposed at the distal end of the spiral groove 382 or at a location in the vicinity thereof. As a consequence, the first tube 361 is in a forward position, whereas the image sensor 65 is in a location in the vicinity of the distal end of the insert portion 10.

In that state, the objective unit 40 is threadingly engaged with a male thread 361x of the first tube 361. At that time, since the key 16 of the inner tube 12 is inserted in the key groove 361y of the first tube 361, the first tube 361 is prohibited from rotation. As a consequence, by rotating the objective unit 40, the above threading engagement can be progressed. After the completion of the above threading engagement, the second tube 362 is rotated. At that time, since the first tube 361 is prohibited from rotation as previously mentioned, the first tube 361 is moved backwardly under the cam effect of the spiral groove 382 and the pin 381. Before long, the engagement projection 45 of the objective unit 40 is brought into engagement with the engagement projections 15 of the inner tube 12, so that the objective unit 40 and the first tube 361 are restricted from moving backwardly and the objective unit 40 is correctly positioned.

In that state, since the coil spring 370 in a compressed state biases the first tube 361 backwardly, the pin 381 is brought into contact with the wall of the spiral groove 382 and thus the first and second tubes 361 and 362 are supported in the engagement position in a stable manner. It should be noted that this coil spring may be eliminated.

In the endoscope of the seventh embodiment, the objective units 40A and 40B of FIGS. 3 and 4 can also be attached instead of the objective unit 40. Any axial dimensional difference of these objective units can be absorbed by axial movement of the first tube 361, and the objective unit can correctly be positioned in a predetermined location.

Figure 18:
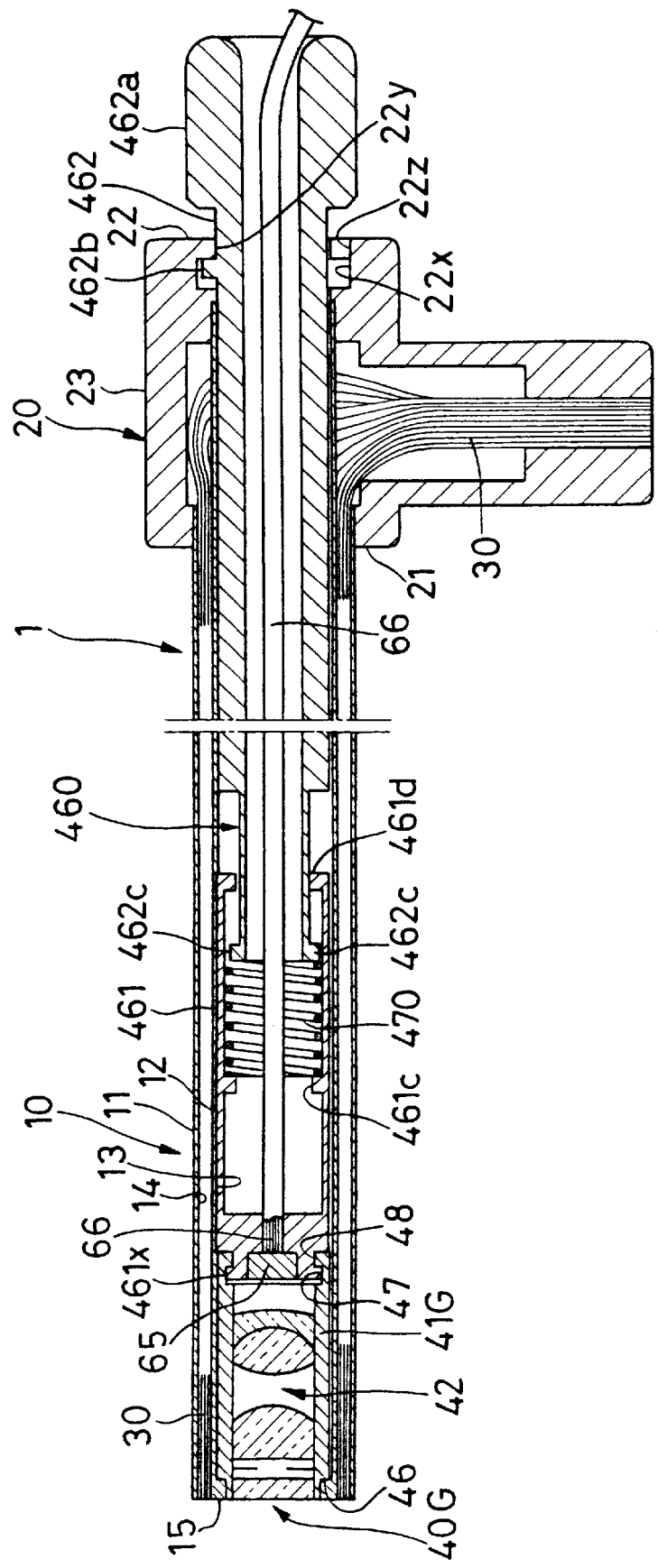
FIG. 18 is a vertical sectional view of the endoscope attached with the objective unit in the eighth embodiment.

In the eighth embodiment shown in FIGS. 17 and 18, the same body 1 as in the sixth embodiment of FIGS. 13 and 14 is used. A holder 460 (retainer means) includes a first tube 461 (first holder member) disposed at a front part of the body 10, and a second tube 462 (second holder member) disposed at a rear part of the body 10.

The first tube 461 has a recess 461*a* for receiving therein an image sensor 65 which recess 461*a* is formed on a distal end face of the first tube 461, and a hole 461*b* for allowing the passage of signal lines 66. A pair of radially outwardly projecting engagement projections 461*x* are formed on a distal end portion of the first tube 461. An annular spring retainer 461*c* is formed on an inner periphery of an intermediate portion of the first tube 461, whereas a pair of radially inwardly projecting engagement projections 461*d* are formed on a rear end thereof.

The second tube 462 has a handle portion 462*a* on a rear end thereof. An engagement projection 462*b* (retainer means) is disposed at location in the vicinity of this handle portion 462*a*. The engagement projection 462*b* can be received in an annular groove 22*x* formed in an inner peripheral surface of an attachment hole 22*a* of a base 20. A radially outwardly projecting annular spring retainer 462*c* is formed on a distal end of the second tube 462. A pair of axially extending passage grooves (not shown) are formed in the spring retainer 462*c*. While allowing the passage of the engagement projections 461*d* of the first tube 461 in the passage groove of the spring retainer 462*c*, the distal end portion of the second tube 462 is inserted into the rear end portion of the first tube 461. Thereafter, by rotating the second tube 462, the engagement projections 461*d* and the spring retainer 462*c* are brought into engagement with each other, so that the second tube 462 is prevented from coming off. A coil spring 470 is received in the rear end portion of the first tube 461. Opposite ends of this coil spring 470 are in abutment with the spring retainers 461*c* and 462*c*.

An objective unit 40G used in this embodiment, unlike the afore-mentioned objective unit, has a support 41G whose distal end is reduced in diameter and provided with a step 46. An annular groove 47 is formed at a location in the vicinity of a rear end of the support 41G, and an annular engagement projection 48 is disposed adjacent to the annular groove 47. A pair of axially extending passage grooves (not shown) are formed in the engagement projection 48.

In this embodiment, first, as shown in FIG. 17(B), the objective unit 40G and the holder 460 is connected together. That is, the engagement projection 461*x* formed on the distal end of the first tube 461 is allowed to pass through the passage groove formed in the engagement projection 48 on the rear end of the objective unit 40G. When the engagement projection 461*x* is brought to the annular groove 47 of the objective unit 40G, the objective unit 40G is rotated by 180 degrees. By doing this, the engagement projections 461*x* and 48 are engaged with each other and as a consequence, the objective unit 40G and the first tube 461 are connected together.

Then, the connected objective unit 40G and holder 460 are inserted from back of the body 1. Before long, as shown in FIG. 18, the step 46 of the objective unit 40G is brought into abutment with the engagement projection 15 formed on the distal end of the insert portion 10 and correctly positioned. When the second tube 462 of the holder 460 is pushed in against the coil spring 470, the engagement projection 462*b* is allowed to pass through the passage groove 22*z* of the base portion 20 and brought to the annular groove 22*x*. Thereafter, by rotating the second tube 462, the engagement projection 462*b* is brought into engagement with the engagement projection 22*y*. In that state, the holder 460 is biased to be elongated under the effect of the coil spring 470 in a compressed state. That is, the first tube 461 is biased forwardly, while the second tube 462 is biased backwardly. The first tube 461 is prohibited from moving forwardly by engagement between the step 46 of the objective unit 40G and the engagement projection 15 of the distal end portion of the insert portion 10. The second tube 462 is brought into engagement with the base portion 20 by the engagement between the engagement projections 462*b* and 22*y*. Since the second tube 462 is prohibited from moving backwardly, the holder 460 is supported in a stable manner. Accordingly, the objective unit 40G and the image sensor 65 are supported in a stable manner.

In the endoscope of the seventh embodiment, a wide angle objective unit having different axial dimension or the like can also be used instead of the objective unit 40G. Any axial dimensional difference of the objective units can be absorbed by axial movement of the first tube 461 accompanied by variation of the length of the coil spring 470, and the objective unit can be attached to a predetermined location.

In the ninth embodiment shown in FIGS. 19, 20 and 21, a holder 560 (retainer means) is very short compared with the insert portion 10 and disposed at a distal end portion of the insert portion 10. As shown in FIG. 19, the holder 560 has a recess 560*a* for receiving therein an image sensor 65 which recess 560*a* is formed on a distal end face of the holder 560, and a hole 560*b* for allowing the passage of signal lines 66. An axially extending key groove 560*c* is formed in an outer periphery of the holder 560. A key 16 formed on the inner tube 12 is inserted into the key groove 560*c*. Owing to this arrangement, the holder 560 is prevented from rotating.

A coil spring 570 is interposed between a rear end of the holder 560 and a spring retainer 17 formed on the inner tube 12. The holder 560 is biased forwardly by the force of this coil spring 570. When the objective unit is not yet attached, the distal end of the holder 560 is brought into engagement with the engagement projection 15 on the distal end of the inner tube 12.

As shown in FIG. 20, a support 41H of an objective unit 40H used in this embodiment has no connection means with respect to the holder 560. An axially extending passage groove 49 is formed in an outer periphery of the support 41H. A pair of projecting hook portions 44 are formed on a distal end face of the support 41H. An annular step 46 is formed at a location in the vicinity of the distal end of the support 41H.

With the above construction, as shown in FIG. 21, the objective unit 40H is inserted through a distal end opening of the first receiving space 13 against the coil spring 570. At that time, passage of the engagement projection 15 within the passage groove 49 makes it possible for the objective unit 40H to be inserted. When the engagement projection 15 is disengaged from the distal end of the passage groove 49, the engagement projection 15 and the step 46 can be brought into engagement with each other by rotating the objective unit 40H with a finger hooked on the hook portion 44. In that state, the holder 560 and the objective unit 40H are biased forwardly by the effect of the coil spring 570 in a compressed state. Moreover, the objective unit 40H is engaged with the distal end portion of the insert portion 10 and prohibited from moving forwardly. Accordingly, the holder 560 and the objective unit 40H are contacted with each other under the effect of the coil spring 570 and supported in a stable manner.

In the endoscope of the ninth embodiment, wide angle objective unit having a different axial direction, or the like can also be used instead of the objective unit 40H. Any axial dimensional difference of the objective units can be absorbed by axial movement of the holder 560 accompanied by variation of the length of the coil spring 570, and the objective unit can be attached to a predetermined location.

Figure 22:
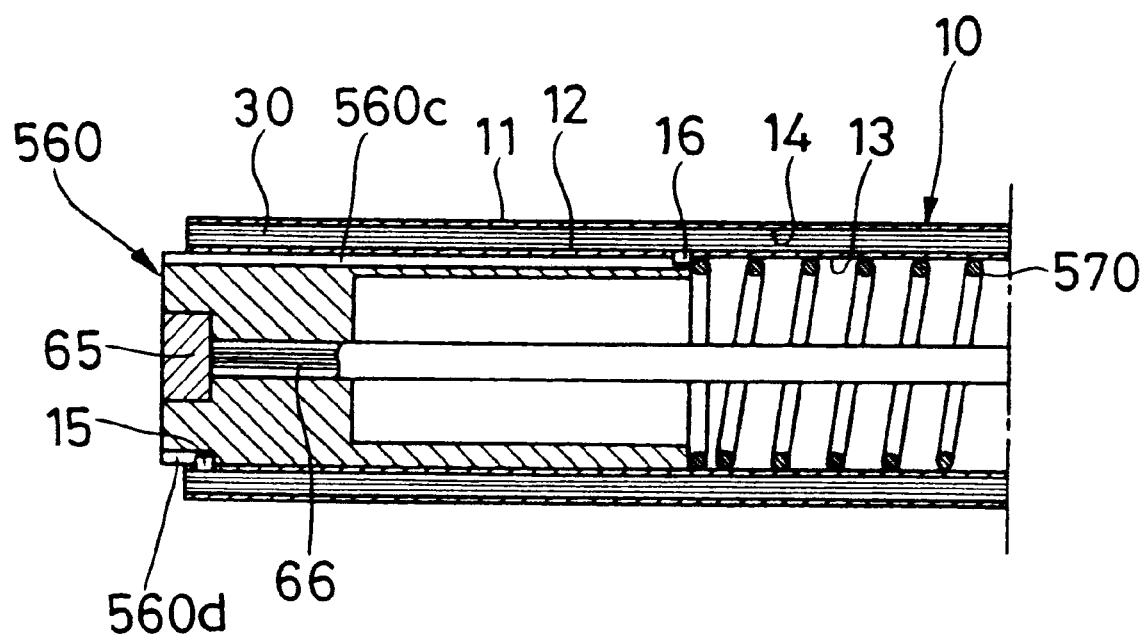
FIG. 22 is a vertical sectional view showing a distal end portion of an endoscope without being attached with an objective unit according to the tenth embodiment of the present invention.

The tenth embodiment shown in FIG. 22 is basically the same as the ninth embodiment shown in FIGS. 19 through 21. Only difference is that an axially extending groove 560d is formed in an outer periphery of a distal end portion of a holder 560 at a location radially opposing a passage groove 560c. When an objective unit is not yet attached, the engagement projection 15 enters the groove 560d. Accordingly, the distal end portion of the holder 560 is allowed to project forwardly and therefore, an image sensor 65 can easily be cleaned.

In the eleventh embodiment shown in FIG. 23, there is provided a flexible endoscope. This endoscope basically resembles the ninth embodiment of FIGS. 19 through 21. Only difference is that an insert portion 10L is flexible and thus can be bent in operation. More specifically, a body 1L includes an insert portion 10L and a hollow base portion 20L disposed at a rear end of the insert portion 10L. The insert portion 10L includes a flexible portion $10L_1$ occupying a large part of its entire length, a bendable portion $10L_2$ extending from a distal end of the flexible portion $10L_1$, and a hard distal end portion $10L_3$ extending from a distal end of the bendable portion $10L_2$. The flexible portion $10L_1$, includes a flex tube formed by spirally winding a belt plate, a braid (both not shown) disposed on outer periphery of the flex tube, and a resin tube 100 disposed on the outer periphery of the braid. The bendable portion $10L_2$ is constituted of a plurality of joint rings 101 rotatably connected together, a braid (not shown) disposed on the outer periphery of the joint rings 101, and the resin tube 100 disposed on the outer periphery of the braid. The bendable portion $10L_2$ is also flexible. The foremost joint ring 101 is connected with a distal end of a wire 102. A rear end of this wire 102 is connected to a control member 103 disposed on the base portion 20L. By rotating this control member 103, the bendable portion $10L_2$ can be bent.

The distal end portion $10L_3$ is formed of an elongated hard member 110. A first receiving space 13L and a second receiving space 14L are formed in this hard member 110. The foremost end joint ring 101 is connected to a rear end portion of the tube 110. The holder 560 and the objective unit 40H received in the tube 110 are almost the same as those of the ninth embodiment. Therefore, like parts are denoted by like reference numeral and detailed description thereof is omitted.

In the eleventh embodiment, utilizing the advantages in that the holder 560 is short and the objective unit 40H can be attached from the distal end opening of the receiving space 13L, the insert portion 10L can be made flexible.

The unique points in the above-mentioned embodiments can, in principle, be applied to other embodiments.

It should be noted that the image transmission means may be an optical fibers bundle. In that case, a distal end face of the optical fibers bundle serves as light receiving means. The base portion may be provided with an ocular portion so that an image coming from the optical fibers bundle can be seen.

What is claimed is:
1. An endoscope comprising:
   (a) a body including a hollow insert portion, said insert portion being elongate and having a hard distal end portion;
   (b) illumination light transmission means whose distal end portion is disposed within the distal end portion of said insert portion and extending backwardly through said insert portion;
   (c) an objective optical system disposed within the distal end portion of said insert portion;
   (d) light receiving means disposed within said insert portion behind said objective optical system, and adapted to receive reflected light from an observation object via said objective optical system;
   (e) image transmission means for backwardly transmitting image information received by said light receiving means, said image transmission means being inserted through said insert portion;
   (f) an objective unit including said objective optical system, and a sleeve-like support for receiving and supporting said objective optical system, said objective unit being detachably supported within the distal end portion of said insert portion; and
   (g) retainer means for retaining said light receiving means within said insert portion, so that an axial position of said light receiving means is adjustable in accordance with an axial dimension of said objective unit, wherein said retainer means has a holder extending in an axial direction of said insert portion and adapted to hold said light receiving means at a distal end portion of said holder, said insert portion including a first and a second receiving space formed in the distal end portion thereof, said first and second receiving spaces being allowed to extend in the axial direction and partitioned with each other, said first receiving space being opened at a distal end face of said insert portion, said objective unit and said holder being slidably received in said first receiving space, the distal end portion of said illumination light transmission means being received in said second receiving space, wherein the distal end portion of said holder and a rear end portion of said support are detachably connected with each other by connection means, and wherein said connection means includes a first engagement projection formed on an inner periphery of selected one of the rear end portion of said support and the distal end portion of said holder and projecting radially inwardly, and a second engagement projection formed on an outer periphery of the remainder and projecting radially outwardly, selected one of said first and second engagement projections extending in a circumferential direction and formed in a part thereof with an axially extending passage groove for allowing the passage of the remaining engagement projection.

2. An endoscope comprising:
   (a) a body including a hollow insert portion, said insert portion being elongate and having a hard distal end portion;

b) illumination light transmission means whose distal end portion is disposed within the distal end portion of said insert portion and extending backwardly through said insert portion;

(c) an objective optical system disposed within the distal end portion of said insert portion;

(d) light receiving means disposed within said insert portion behind said objective optical system, and adapted to receive reflected light from an observation object via said objective optical system;

(e) image transmission means for backwardly transmitting image information received by said light receiving means, said image transmission means being inserted through said insert portion;

(f) an objective unit including said objective optical system, and a sleeve-like support for receiving and supporting said objective optical system, said objective unit being detachably supported within the distal end portion of said insert portion; and (g) retainer means for retaining said light receiving means within said insert portion, so that an axial position of said light receiving means is adjustable in accordance with an axial dimension of said objective unit, wherein said retainer means has a holder extending in an axial direction of said insert portion and adapted to hold said light receiving means at a distal end portion of said holder, said insert portion including a first and a second receiving space formed in the distal end portion thereof, said first and second receiving spaces being allowed to extend in the axial direction and partitioned with each other, said first receiving space being opened at a distal end face of said insert portion, said objective unit and said holder being slidably received in said first receiving space, the distal end portion of said illumination light transmission means being received in said second receiving space, wherein said endoscope further comprises engagement means, said engagement means having an engagement projection formed on an inner peripheral surface of a distal end portion of said first receiving space of said insert portion and projecting radially inwardly, the distal end of said support being brought into engagement with said engagement projection to restrict forward movement of said objective unit so that said objective unit is correctly positioned, and wherein an axially extending passage groove is formed in an outer peripheral surface of said support adapted to allow the passage of said engagement projection when said objective unit is inserted into said insert portion.

3. An endoscope comprising:

(a) a body including a hollow insert portion, said insert portion being elongate and having a hard distal end portion;

(b) illumination light transmission means whose distal end portion is disposed within the distal end portion of said insert portion and extending backwardly through said insert portion;

(c) an objective optical system disposed within the distal end portion of said insert portion;

(d) light receiving means disposed within said insert portion behind said objective optical system, and adapted to receive reflected light from an observation object via said objective optical system;

(e) image transmission means for backwardly transmitting image information received by said light receiving means, said image transmission means being inserted through said insert portion;

(f) an objective unit including said objective optical system, and a sleeve-like support for receiving and supporting said objective optical system, said objective unit being detachably supported within the distal end portion of said insert portion; and (g) retainer means for retaining said light receiving means within said insert portion, so that an axial position of said light receiving means is adjustable in accordance with an axial dimension of said objective unit, wherein said retainer means has a holder extending in an axial direction of said insert portion and adapted to hold said light receiving means at a distal end portion of said holder, said insert portion including a first and a second receiving space formed in the distal end portion thereof, said first and second receiving spaces being allowed to extend in the axial direction and partitioned with each other, said first receiving space being opened at a distal end face of said insert portion, said objective unit and said holder being slidably received in said first receiving space, the distal end portion of said illumination light transmission means being received in said second receiving space, and wherein said insert portion is hard over an entire length thereof, said body has a hollow base portion disposed on a rear end of said insert portion, and said holder includes a first holder member for supporting said light receiving means at a distal end portion thereof and extending in the axial direction of said insert portion and a second holder member disposed backwardly of said first holder member and extending axially of said insert portion, a rear end portion of said support of said objective unit and a distal end portion of said first holder member being detachably connected with each other by connection means, a rear end portion of said first holder member being associated with a distal end portion of said second holder member by a spring, said first holder member being biased backwardly and said second holder member being biased forwardly by said spring, so that said objective unit is brought into engagement with the distal end portion of said insert portion by first engagement means to correctly position said objective unit and prohibit said objective unit from being moved backwardly, and so that said second holder member is brought into engagement with said base portion by second engagement means and prohibited from being moved forwardly.

4. An endoscope according to claim 3, in which said first and second holder members each have a tubular configuration, selected one of the rear end portion of said first holder member and the distal end portion of said second holder member being inserted into the remaining one, said spring being interposed between spring retainers formed respectively on the rear end of said first holder member and the distal end of said second holder member, said image transmission means being allowed to extend through interiors of said first and second holder members.

5. An endoscope according to claim 4, in which said second engagement means has an engagement projection formed on the outer periphery of said second holder member and extending radially outwardly, said engagement projection being brought into abutment with a rear face of said base portion to thereby retain said second holder member, an axially extending passage groove being formed in an inner peripheral surface of said base portion adapted to allow the passage of said engagement projection, said second holder member being provided with a pressure projection radially projecting from the distal end portion of said second holder member, said pressure projection being brought into abutment with the rear end of said first holder member when second member is moved forwardly.

6. An endoscope according to claim 3 or 4, in which said second engagement means has an engagement projection formed on the outer periphery of said second holder member and extending radially outwardly, said engagement projection being brought into abutment with a rear face of said base portion to thereby retain said second holder member, an axially extending passage groove being formed in an inner peripheral surface of said base portion adapted to allow the passage of said engagement projection, said second holder member being provided with a pressure projection radially projecting from the distal end portion of said second holder member, said pressure projection being brought into abutment with the rear end of said first holder member when second member is moved forwardly.

7. An endoscope comprising:
(a) a body including a hollow insert portion, said insert portion being elongate and having a hard distal end portion;
(b) illumination light transmission means whose distal end portion is disposed within the distal end portion of said insert portion and extending backwardly through said insert portion;
(c) an objective optical system disposed within the distal end portion of said insert portion;
(d) light receiving means disposed within said insert portion behind said objective optical system, and adapted to receive reflected light from an observation object via said objective optical system;
(e) image transmission means for backwardly transmitting image information received by said light receiving means, said image transmission means being inserted through said insert portion;
(f) an objective unit including said objective optical system, and a sleeve-like support for receiving and supporting said objective optical system, said objective unit being detachably supported within the distal end portion of said insert portion; and
(g) retainer means for retaining said light receiving means within said insert portion, so that an axial position of said light receiving means is adjustable in accordance with an axial dimension of said objective unit, wherein said retainer means has a holder extending in an axial direction of said insert portion and adapted to hold said light receiving means at a distal end portion of said holder, said insert portion including a first and a second receiving space formed in the distal end portion thereof, said first and second receiving spaces being allowed to extend in the axial direction and partitioned with each other, said first receiving space being opened at a distal end face of said insert portion, said objective unit and said holder being slidably received in said first receiving space, the distal end portion of said illumination light transmission means being received in said second receiving space, and wherein said insert portion is hard over an entire length thereof, said body has a hollow base portion disposed on a rear end of said insert portion, and said holder extends through said insert portion and said base portion and projects backwardly of said base portion, a spring being interposed between a spring retainer formed on an inner periphery of said first receiving space and another spring retainer formed on an outer periphery of said holder, said holder being biased backwardly by said spring, a rear end portion of said support of said objective unit and a distal end portion of said first holder member being detachably connected with each other by connection means, said objective unit being retained at the distal end portion of said insert portion by engagement means, so that said objective unit is prohibited from being moved backwardly.

8. An endoscope comprising:
(a) a body including a hollow insert portion, said insert portion being elongate and having a hard distal end portion;
(b) illumination light transmission means whose distal end portion is disposed within the distal end portion of said insert portion and extending backwardly through said insert portion;
(c) an objective optical system disposed within the distal end portion of said insert portion;
(d) light receiving means disposed within said insert portion behind said objective optical system, and adapted to receive reflected light from an observation object via said objective optical system;
(e) image transmission means for backwardly transmitting image information received by said light receiving means, said image transmission means being inserted through said insert portion;
(f) an objective unit including said objective optical system, and a sleeve-like support for receiving and supporting said objective optical system, said objective unit being detachably supported within the distal end portion of said insert portion; and
(g) retainer means for retaining said light receiving means within said insert portion, so that an axial position of said light receiving means is adjustable in accordance with an axial dimension of said objective unit, wherein said retainer means has a holder extending in an axial direction of said insert portion and adapted to hold said light receiving means at a distal end portion of said holder, said insert portion including a first and a second receiving space formed in the distal end portion thereof, said first and second receiving spaces being allowed to extend in the axial direction and partitioned with each other, said first receiving space being opened at a distal end face of said insert portion, said objective unit and said holder being slidably received in said first receiving space, the distal end portion of said illumination light transmission means being received in said second receiving space, and wherein said insert portion is hard over an entire length thereof, said body has a hollow base portion disposed on a rear end of said insert portion, and said holder includes a tubular first holder member for supporting said light receiving means on a distal end portion thereof and extending axially of said insert portion, and a tubular second holder member disposed backwardly of said first holder member, extending axially of said insert portion and projecting backwardly of said base portion, a rear end portion of said support of said objective unit and a distal end portion of said first holder member being detachably connected with each other by connection means, a rear end portion of said first holder member and a distal end portion of said second holder member being connected by a cam mechanism, said cam mechanism including a spiral groove and a projection, said spiral groove formed in selected one of the rear end portion of said first holder member and a distal end portion of said second holder member, said projection being disposed on the remainder and fitted into said spiral groove, said first holder member being axially movably but unrotatably supported by said insert portion, said second holder member being rotatably but axially unmovably supported by said base portion.

9. An endoscope comprising:

(a) a body including a hollow insert portion, said insert portion being elongate and having a hard distal end portion;

(b) illumination light transmission means whose distal end portion is disposed within the distal end portion of said insert portion and extending backwardly through said insert portion;

(c) an objective optical system disposed within the distal end portion of said insert portion;

(d) light receiving means disposed within said insert portion behind said objective optical system, and adapted to receive reflected light from an observation object via said objective optical system;

(e) image transmission means for backwardly transmitting image information received by said light receiving means, said image transmission means being inserted through said insert portion;

(f) an objective unit including said objective optical system, and a sleeve-like support for receiving and supporting said objective optical system, said objective unit being detachably supported within the distal end portion of said insert portion; and (g) retainer means for retaining said light receiving means within said insert portion, so that an axial position of said light receiving means is adjustable in accordance with an axial dimension of said objective unit, wherein said retainer means has a holder extending in an axial direction of said insert portion and adapted to hold said light receiving means at a distal end portion of said holder, said insert portion including a first and a second receiving space formed in the distal end portion thereof, said first and second receiving spaces being allowed to extend in the axial direction and partitioned with each other, said first receiving space being opened at a distal end face of said insert portion, said objective unit and said holder being slidably received in said first receiving space, the distal end portion of said illumination light transmission means being received in said second receiving space, and wherein said insert portion is hard over an entire length thereof, said body has a hollow base portion disposed on a rear end of said insert portion, and said holder includes a first holder member for supporting said light receiving means on a distal end portion thereof and extending axially of said insert portion, and a second holder member disposed backwardly of said first holder member, extending axially of said insert portion and projecting backwardly of said base portion, a rear end portion of said support of said objective unit and a distal end portion of said first holder member being detachably connected with each other by connection means, a rear end portion of said first holder member and a distal end portion of said second holder member being associated with each other by a spring, said first holder member being biased forwardly and said second holder member is biased backwardly by said spring, said objective unit being retained at the distal end portion of said insert portion by first engagement means so that said objective unit is correctly positioned and prohibited from being moved forwardly, said second holder member being detachably retained at said base portion by second engagement means so that said second holder member is prohibited from moving backwardly.

10. An endoscope comprising:

(a) a body including a hollow insert portion, said insert portion being elongate and having a hard distal end portion;

(b) illumination light transmission means whose distal end portion is disposed within the distal end portion of said insert portion and extending backwardly through said insert portion;

(c) an objective optical system disposed within the distal end portion of said insert portion;

(d) light receiving means disposed within said insert portion behind said objective optical system, and adapted to receive reflected light from an observation object via said objective optical system;

(e) image transmission means for backwardly transmitting image information received by said light receiving means, said image transmission means being inserted through said insert portion;

(f) an objective unit including said objective optical system, and a sleeve-like support for receiving and supporting said objective optical system, said objective unit being detachably supported within the distal end portion of said insert portion; and (g) retainer means for retaining said light receiving means within said insert portion, so that an axial position of said light receiving means is adjustable in accordance with an axial dimension of said objective unit, wherein said retainer means has a holder extending in an axial direction of said insert portion and adapted to hold said light receiving means at a distal end portion of said holder, said insert portion including a first and a second receiving space formed in the distal end portion thereof, said first and second receiving spaces being allowed to extend in the axial direction and partitioned with each other, said first receiving space being opened at a distal end face of said insert portion, said objective unit and said holder being slidably received in said first receiving space, the distal end portion of said illumination light transmission means being received in said second receiving space, and wherein said holder is shorter than said insert portion, a spring retainer is disposed on an inner periphery of said first receiving space and a spring is interposed between said spring retainer and the rear end portion of said holder, said holder and said objective unit to be brought into abutment with said holder being biased forwardly by said spring, said first receiving space being provided on a distal end portion thereof with an engagement projection, a distal end portion of said objective unit being brought into engagement with said engagement projection so that said objective unit is correctly positioned and prohibited from being moved forwardly, an axially extending passage groove for allowing the passage of said engagement projection being formed in an outer peripheral surface of said support of said objective unit.

11. An endoscope according to claim 10, in which said insert portion excepting a distal end portion thereof is flexible.

* * * * *